United States Patent [19]
Dixon

[11] Patent Number: 5,374,250
[45] Date of Patent: Dec. 20, 1994

[54] SAFETY SYRINGE

[76] Inventor: Richard E. Dixon, Rt. 1, Box 9123, Tyler, Tex. 75708

[21] Appl. No.: 146,582

[22] Filed: Nov. 1, 1993

[51] Int. Cl.$^5$ ............................................. A61M 5/00
[52] U.S. Cl. .................... 604/110; 604/198; 604/195; 128/763
[58] Field of Search .......... 604/110, 195, 187, 198, 604/263; 128/763-765

[56] References Cited

U.S. PATENT DOCUMENTS

| | | | |
|---|---|---|---|
| 4,681,567 | 7/1987 | Masters et al. | 604/198 |
| 4,738,663 | 4/1988 | Bogan | 604/198 |
| 4,834,718 | 5/1989 | McDonald | 604/195 |
| 4,932,945 | 6/1990 | Braginetz et al. | 604/195 |
| 4,946,446 | 8/1990 | Vadher | 604/198 |
| 4,973,316 | 11/1990 | Dysarz | 604/187 |
| 5,019,051 | 5/1991 | Hake | 604/198 |
| 5,032,117 | 7/1991 | Motta | 604/88 |
| 5,088,986 | 2/1982 | Nusbaum | 604/187 |
| 5,092,853 | 3/1992 | Couvertier, II | 604/195 |
| 5,114,410 | 5/1992 | Caralt Batlle | 604/195 |
| 5,120,310 | 6/1992 | Shaw | 604/195 X |
| 5,246,428 | 9/1993 | Falknor | 604/198 |
| 5,267,973 | 12/1993 | Haber et al. | 604/110 X |

FOREIGN PATENT DOCUMENTS

0396619A1  5/1990  European Pat. Off.
2243552A  11/1991  United Kingdom.

*Primary Examiner*—John D. Yasko
*Attorney, Agent, or Firm*—Ronald B. Sefrna; Charles W. Alworth

[57] ABSTRACT

Three versions of a safety syringe are disclosed which can be used as a Pressure Sampler syringe, an Aspiration Sampler syringe, or a regular Hypodermic Injection syringe. The device has a manually retractable needle which withdraws to inside the syringe after use; thus, protecting the user from accidental stabbing by an exposed used needle. The syringe plunger can still function to expel entrained fluids after the used needle is retracted to the "safe" position, which allows the syringe to be used as a blood gas analysis sampler. Additionally the sampler versions of the syringe will completely seal the sampled fluid from the atmosphere, thus assuring no contamination of the sample. The device consists of three basic parts, a retractable needle and seal assembly, a standard syringe barrel, and a modified plunger which stores the retracted needle.

30 Claims, 19 Drawing Sheets

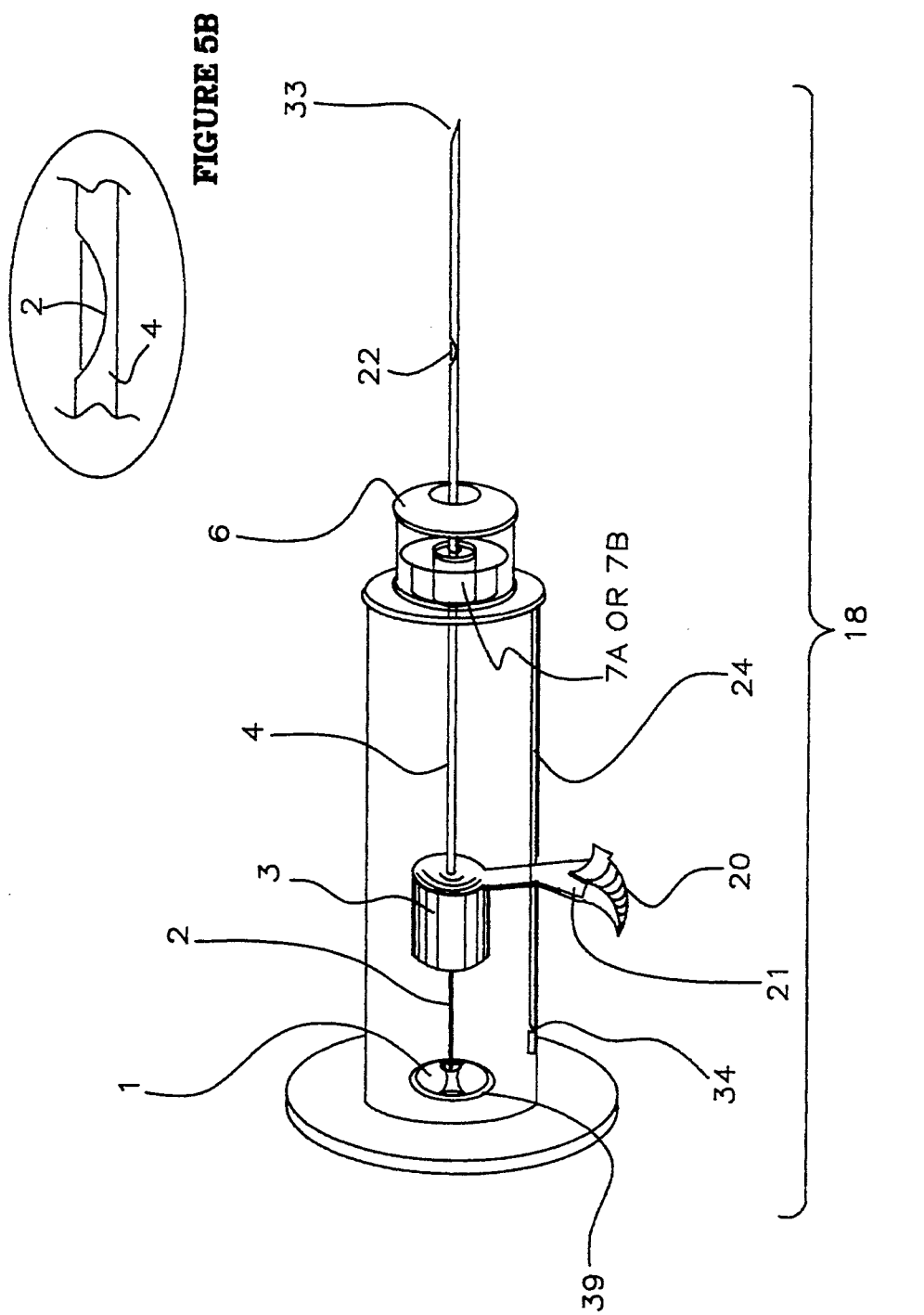

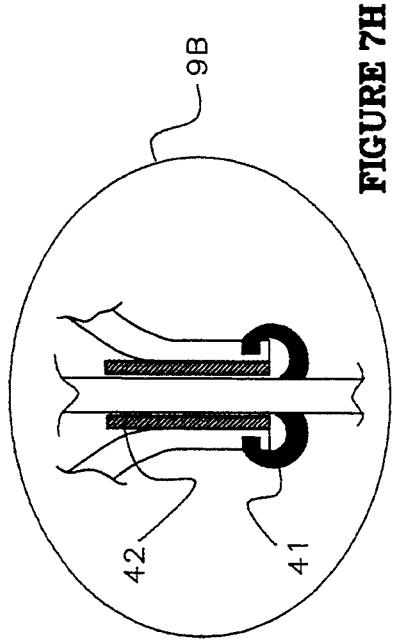
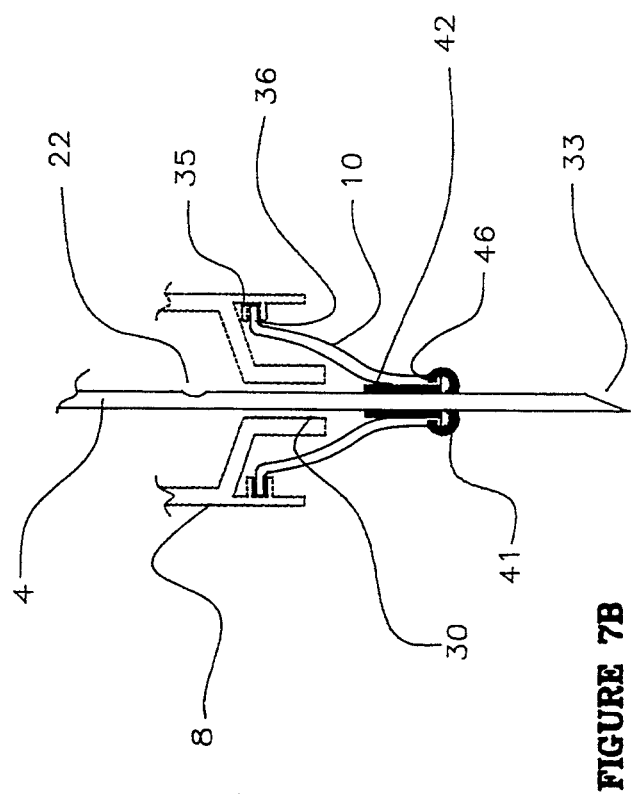
FIGURE 7H
FIGURE 7B

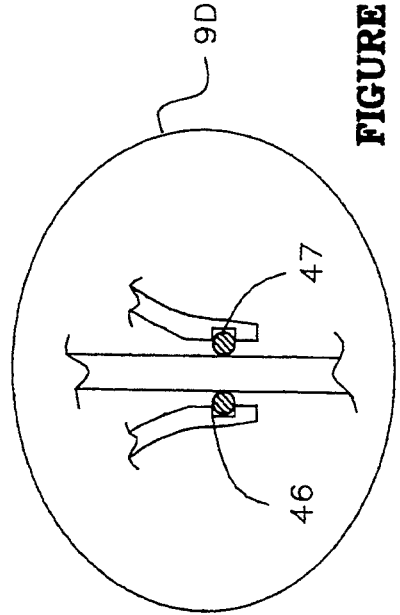
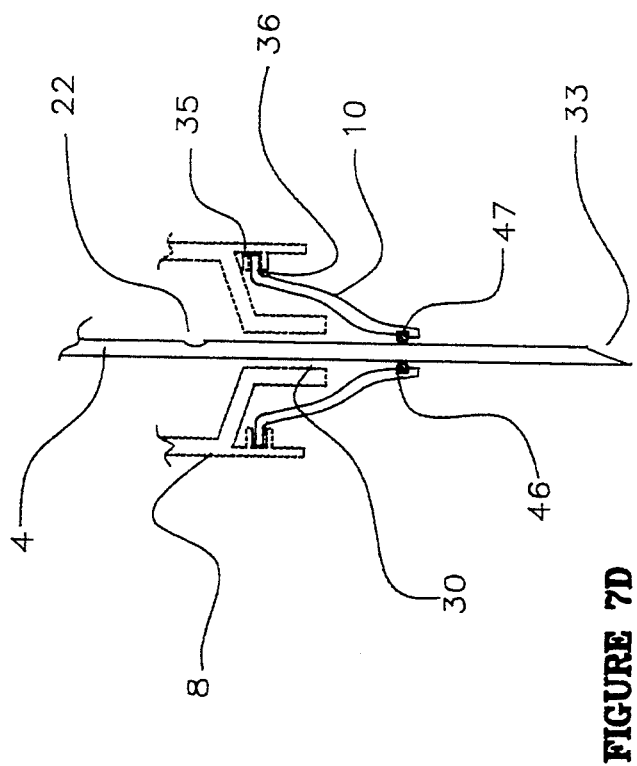
FIGURE 7J
FIGURE 7D

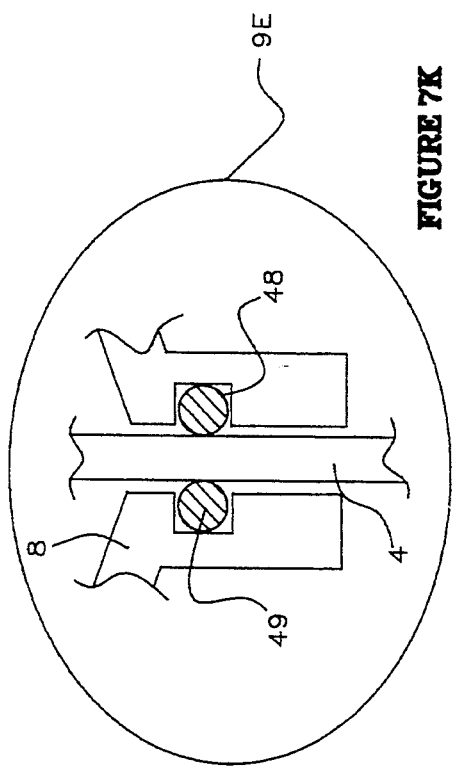
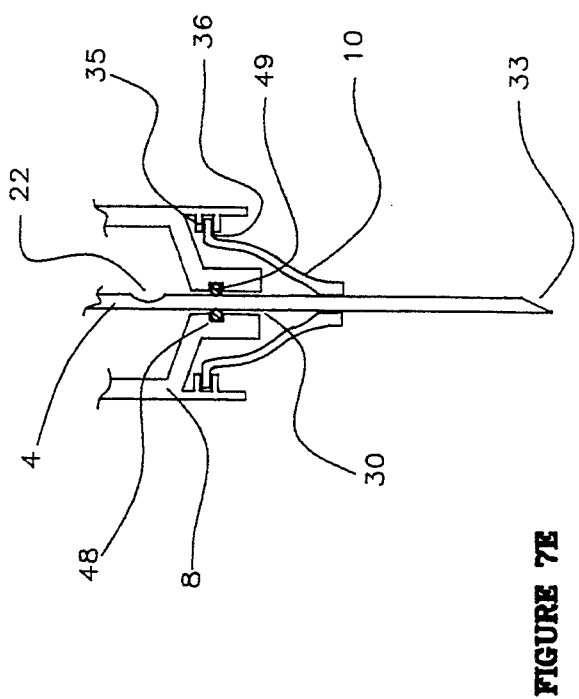
FIGURE 7K
FIGURE 7E

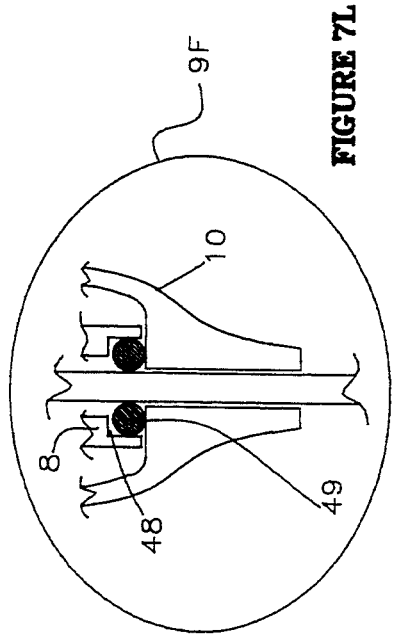
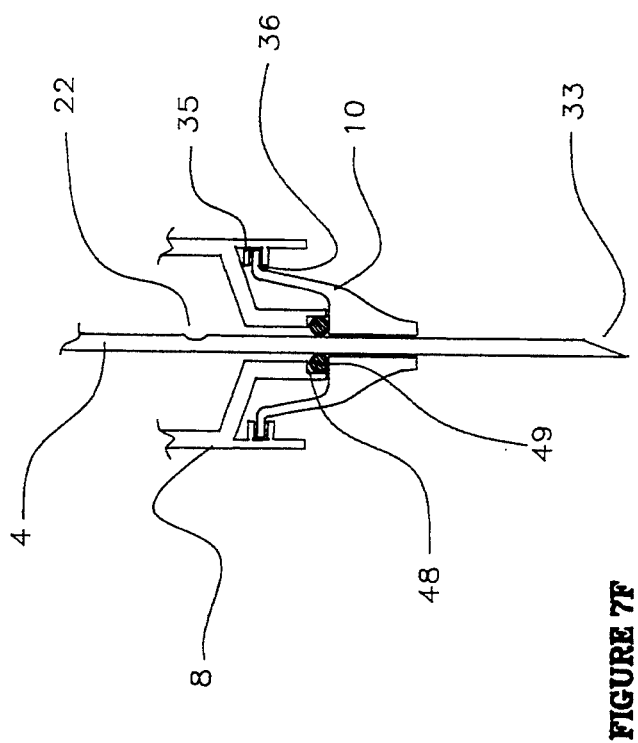

SAFETY SYRINGE

TECHNICAL FIELD OF THE INVENTION

This invention relates to hypodermic syringes and their use in Arterial Blood Gas Analysis. In particular it relates to a syringe that will safely sheath the needle after drawing blood to protect a worker and still allow the syringe to inject its sample into an Arterial Blood Gas Analysis Machine with the needle sheathed. The device could easily find use as a regular hypodermic syringe containing an easily sheathed needle.

BACKGROUND OF THE INVENTION

Hypodermic syringes have been used in medicine for countless years. They find use for the injection of fluids into the body and for the removal of sample fluids from the body. Most syringes have a common business end in the form of a sharp needle. For as long as syringes have been used, countless medical workers have been accidently picked by an exposed needle. An accidental pricking causes little harm if and only if the needle has not been contaminated by being inserted into a body otherwise the needle would still be sterile (i.e. no germs, no bacteria, no virus, etc. will be present on the needle). The major concern occurs if the accidental pricking of the medical worker occurs after the needle has been inserted into a body. Today's major dread is exposure to HIV, although exposure to Hepatitis B should not be overlooked.

There have been many efforts by previous medical workers to devise a safe and certain method for sheathing a needle after its use and before the syringe has been properly disposed. These methods or inventions have taken two avenues:

1) an external sliding sheath that covers the needle, and 2) a system to retract the needle into the body of the syringe.

The simplest devices have been those that externally sheath the needle while the most complex have been those that retract the used needle. All of these safety devices must have a positive locking device to either keep the guard (or sheath) in place or keep the retracted needle in place within the body of the syringe.

Generally the sheathing devices use an external catch or tab molded onto the outside of the syringe body. This results in a distortion of the circular shape of the syringe and makes it almost impossible to insert into another instrument, such as a Blood Gas Analysis Machine, so the body sample contained within the syringe can be safely and hygienically injected into that instrument. Generally speaking, in these externally guarded syringes the sheath must be withdrawn to allow re-injection of the sample; thus the worker is again exposed to a prickly potential.

The devices which use a retractable needle generally accomplish their purpose by using a loaded spring and latches within the syringe. Thus after the syringe is used, the plunger is pushed harder or a latch is pressed and the needle "shoots" back inside the syringe body. This technique appears to work in spite of the number of parts and the potential for an unwanted retraction. Unfortunately if these devices were to be used for Blood Gas Analysis or any analysis that requires the taking of a body sample for re-injection into a machine, the retracted needle will interfere with the release of the sample. That is, with the needle firmly wedged inside the body of the syringe, the plunger cannot move back into the body of the syringe and force the sample out of the syringe.

An object of this invention is to make available a safety syringe in which the needle can be retracted into the body of the syringe after use and yet not interfere with the operation of the syringe when it is used to collect body samples; yet be capable of regular use. Another object of the invention was to provide a syringe that was easy to manufacture and did not use a loaded spring to retract the needle; thus making accidental retraction impossible. Furthermore, the syringe becomes perfectly safe after needle retraction and cannot accidently prick a worker in the laboratory when a body sample is being injected into an analysis machine. In addition, by using a retractable needle, the syringe retains its standard circular shape and will fit into any of the standard laboratory analysis machines. Finally, because the actual needle retracts out of the way, "the nipple" of the syringe is safely available for attachment to analysis machines—this is the preferred method of attachment to such machines.

PRIOR ART

Examples of safety syringes that use external sheathing can be found in U.S. Pat. Nos. 4,681,567; 4,738,663; 5,019,051; and 5,088,896 and in European Patent Application 0,369,619. This form of the prior art will be the first to be examined.

U.S. Pat. No. 4,681,567 (Masters et al.) discloses a cumbersome external sheath or guard. The sheath guide mechanism distorts the circular outside of the syringe body in such a manner that it would be impossible to insert the syringe into a laboratory analysis machine. The only way to use this device would be to unsheathe the needle, which is very easy, and inject fluid via the needle. The exposed needle would offer a serious prickly potential the medical worker or technician.

U.S. Pat. No. 4,738,663 (Bogan) is an "improvement" on Masters in that the sheathed needle cannot readily be exposed. This disclosure works well for a standard hypodermic syringe which is used ONLY to give injections but will not work well for sample syringes in that the sheath will interfere with an analysis machine. Furthermore, since the sheath cannot be retracted the syringe really cannot be used as a sample syringe or collection device.

U.S. Pat. No. 5,019,051 (Hake) is another variation of the external sheath guard concept. Here again the external sheath would interfere with an analysis machine whenever the sample was re-injected. U.S. Pat. No. 5,088,986 (Nusbaum) discloses a spring loaded slidable sheath. Its external locking tabs greatly distort the tube-like structure of the syringe body and would interfere with any analysis machine. The device could be used with an analysis machine but only if the needle were re-exposed. Thus the worker could again be exposed to a prickly potential.

In a similar manner, the European Disclosure 0,369,619 (Ogie & Braddock), would interfere with the analysis machine. Once more this disclosure can re-expose the needle to the laboratory worker with the corresponding prickly potential.

Examples of needle retraction devices can be found in U.S. Pat. Nos. 4,834,718; 4,932,945; 4,946,446; 4,973,316; 5,032,117; 5,092,853; and 5,114,410, and in British Patent 2,243,552,A. We will now examine this type of protection.

U.S. Pat. No. 4,834,718 (McDonald) discloses a retractable needle and catheter system. The retractable needle operates in conjunction with a catheter and is meant to puncture the skin to allow the catheter to enter a body. Once the catheter is in place the needle is withdrawn into the device and the needle/sheath device is disengaged from the catheter. This leaves the catheter in place and the puncture device in a safe state. It is absolutely impossible for this disclosure to act as a syringe for it can neither inject fluids nor withdraw fluids.

U.S. Pat. No. 4,932,945 (Braginetz et al.) also discloses a catheter insertion device with a retractable needle. This disclosure is similar to that of McDonald but adds a self sealing bushing to prevent back-flow of body fluids into the insertion housing. The insertion needle punctures the bushing and passes though the catheter housing, upon withdrawal of the needle the bushing closes off to stop any fluids from moving into the needle housing (see claim 10).

U.S. Pat. No. 4,946,446 (Vadher) discloses a spring loaded needle retraction system. The needle retraction system actually is a needle and spring loaded retraction sheath that attaches to a regular syringe via the "Luer-Lock" or nipple. Essentially the device works somewhat like the retraction mechanism in a ballpoint pen. There is a rotational cam which holds the needle extended while the shot is administered; upon twisting the plunger to one side the cam rotates and the needle is automatically retracted into the housing. The device can be used to draw blood for Blood Gas Analysis machines, but suffers from the fact that the syringe cannot be shut off from the atmosphere. Thus the blood sample can be contaminated or outgas while the sample is being transported to the laboratory. Outgas is a term of art that means that the sample will allow entrained gases to be released, thus the sample will no longer contain the same volume of gases as when the sample was first taken; whereas contamination would that the sample would absorb gases from the atmosphere. Another drawback is that the needle system when attached to a syringe will be inordinately long and difficult to use.

U.S. Pat. No. 4,973,316 (Dysarz) claims to have produced a safety retractable needle injection syringe. When the chamber which holds the injection fluid is full the needle cannot be retracted. Thus if this device is used to obtain samples then the needle must be left exposed. Hence, this device does not provide any protection to the worker in the laboratory.

U.S. Pat. No. 5,032,117 (Motta) appears to use a sheathed needle but the function of this needle is only to vent a gravity feed intravenous delivery system after a measured dose of medication had been delivered by syringe.

U.S. Pat. No. 5,092,853 (Couvertier) discloses yet another spring loaded needle retraction system. The stated purpose of this device is to permanently store the needle after use to protect the medical worker and to prevent further use of the syringe by unauthorized users such as illegal drug addicts. Thus this system is deliberately designed NOT to be used other than as a one time hypodermic syringe. The device cannot be used as a sample syringe. Further the spring/needle latching system causes a distortion of the body of the syringe as that it would be difficult to use in an analysis machine.

U.S. Pat. No. 5,114,410 (Caralt Batlie) discloses a further spring loaded needle retraction system. This disclosure is simpler then the Couvertier syringe and does not distort the outer body of the syringe but when the needle is retracted it is once again impossible to reuse the syringe. This device cannot be used for taking blood samples.

U.K. Patent Application 2,243,552,A (Deighton et al.) discloses one more version of a spring loaded needle retraction system. In this disclosure the needle is manufactured with a slight bend so that when the needle is retracted, after use, the needle cannot possibly be forced out by pressure on the plunger. Thus this system cannot be used for sample collection use as the stored sample could not be ejected.

It is very apparent that the prior art has not considered the use of "safety" syringes for use as a body fluids sample collector, be they the sheathing type or the retraction type. The sheathing devices could possibly work as sample collectors but fail to protect the needle when the sample is being discharged for analysis. The spring loaded retraction systems do not lend themselves to a sample syringe and they suffer from extreme complexity. One further disadvantage for the spring loaded systems is the possible failure of the latch during use which would retract the needle at the wrong time. The instant invention solves all the problems contained within the prior art and solves problems not envisioned by the prior art

SUMMARY OF THE INVENTION

The instant invention is a simple safety syringe utilizing a retractable needle which is stored within the plunger of the syringe. The instant invention may be used as a standard hypodermic syringe or as a sample syringe. The needle retraction system is "on-call", that is to say the user manually retracts the needle into the plunger housing alter using the syringe. There is absolutely no fear of an accidental retraction of the needle while the syringe is in use. The preferred embodiment does not envision reuse of the needle once it is retracted but there is no reason why the device could not be set up to be reusable. For example the syringe could be sent to the user with the needle retracted, the user could extend the needle, the user could employ the device, and then the user could finally retract the used needle.

In order to facilitate the summary of the invention, the simplest embodiment of the invention will be described. The simplest embodiment is the hypodermic injection syringe which for all practical purposes starts with the standard hypodermic barrel; complete with a standard Luer Lock. The plunger of the syringe is modified so that it is a hollow plunger with a slot running its entire length. The retractable needle, which is roughly the same length as the plunger runs through the hollow plunger and out of the end of both the plunger and the barrel of the syringe. The end of the needle that is within the plunger is terminated with a head or cap that has a lever arm that extends out of the slot on the plunger. The hollow needle has a port that would be in communication with the inside of the syringe barrel. The port is positioned so that it is at the extreme bottom (nearest the exposed needle) end of the barrel. This ensures that as the plunger is depressed the fluid in the body would be forced into and through the hollow needle. This of course assumes that the proper seals are in place around the hollow needle and the plunger/piston as well as the barrel nipple and the hollow needle. These sealing arrangements will be discussed.

To keep the retractable needle extended, the lever arm has a latch which can lock over the barrel finger flange. In the extended position, the lever arm latch slides over the barrel flange and keeps the needle extended. The lever arm is free to move within the slot in the plunger and vice versa. Since the plunger is free to rotate within the barrel the lever arm can also rotate. In order to unlatch the needle for retraction, the lever arm is rotated so that the lever arm latch disengages from the barrel finger flange. Note that the barrel finger flange can be manufactured with a slot so that the lever arm latch can clear the flange or the standard syringe that incorporates a flange with two flat sides can be used. If the standard syringe flange incorporating two flat sides is used, the lever arm latch will clear the flange in two places (i.e. the two flats). Once the lever arm latch clears the flange, the lever arm can be moved "upwards" withdrawing the needle into the hollow plunger. The hollow plunger is formed with latching ramps at the top end of the plunger. When the needle head reaches the top of the hollow plunger, the latching ramps will retain the needle head and the needle remains up inside the hollow plunger. The plunger can be pushed down towards the bottom of the syringe barrel, but the needle will not come out because the needle is inside the hollow plunger. Actually, the retracted needle will extend slightly below the piston and into the nipple of the barrel whenever the plunger is completely pushed down towards the bottom of the syringe barrel. Note, the retracted needle will not extend out of the barrel nipple when the plunger is completely pushed down.

This simplified explanation describes one embodiment of the device which envisions the injection hypodermic syringe. When the invention is used as an aspiration sampler, as the plunger is withdrawn, sample fluid would be drawn through the needle and into the barrel. Finally, if the syringe is used as a pressure filled sampler and with the plunger withdrawn to the required sample volume, arterial blood pressure will force the sample into the hollow needle, through the needle port and into the barrel interior. The operation is absolutely the same as a standard syringe or as a standard combined aspirator/pressure sampler. However, when the hypodermic embodiment is used as a sample collector several problems can occur. First, sample fluid can escape through the open end of the barrel at the Luer Lock when the needle is retracted. Second, fluid can pass through the hollow needle and through the .needle port into the plunger and then out of the syringe when the needle is retracted. A second embodiment of the invention solves these problems by adding a seal at the barrel Luer Lock end of the syringe, a valve to close off the needle port when the needle is retracted, and a seal between the hollow plunger and the hollow needle. The barrel Luer Lock end seal may take one of two forms: the seal can be incorporated into the barrel or the seal can be incorporated into a cap that fits into the Luer Lock. The second method is preferred for it means that a standard unmodified syringe barrel may be used, whereas the first method would require another manufacturing step. The needle port valve consists of a solid wire affixed the plunger and over which the hollow needle retracts. As the needle is retracted, the wire stays in place and forces fluid back along the hollow needle, out the port and into the barrel. Eventually the wire passes the needle port effectively blocking the port. This valve system ensures that the sample cannot be contaminated nor can gases contained within the sample outgas. The syringe becomes a completely closed sample vessel: a factor that is critical in Arterial Blood Gas Analysis.

It should also be apparent that a seal arrangement, in all embodiments, will be needed between the hollow needle and the tip of the hollow plunger. This seal can take one of several forms. For example if the device is being used as a pressure filled sampler, then the seal must allow air within the syringe barrel to escape; however, that seal must then stop any fluid from passing. This can be accomplished using a "microfilter" material which is well known in the art. The microfilter will pass air, but when fluid touches the filter it expands and seals. On the other hand if the instant invention is used as an injection syringe or as an aspirator sampler, the seal must be tight at all times. This can be accomplished with the use of proper seals within the hollow plunger or piston. A similar seal arrangement will be needed at the Luer Lock end of the barrel.

BRIEF DESCRIPTION OF THE DRAWINGS

FIG. 5 is a ghost view of the Needle Retraction System, which includes the needle and guide wire/valve assembly, the needle assembly and the plunger assembly.

FIG. 5B is an enlarged view of the needle port showing the needle valve closing off the needle port shown in FIG. 5.

FIG. 7B is a side view of the Aspiration Mode Barrel Needle Seal System.

FIG. 7H is an enlarged view of the barrel needle seal system shown in FIG. 7B.

FIG. 7D is a side view of an alternate embodiment of the Barrel Needle Seal System which would function in all modes.

FIG. 7J is an enlarged view of the barrel needle seal system shown in FIG. 7D.

FIG. 7E is a side view of another alternate Barrel Needle Seal System in which the seal is placed in the barrel of the syringe. Note that a similar seal arrangement could be used to seal the needle in the plunger.

FIG. 7K is an enlarged view of the barrel needle seal system shown in FIG. 7E.

FIG. 7F is a side view of yet another alternate Barrel Needle Seal System in which the seal is placed in the barrel nipple and held in place by a modified Luer Cap.

FIG. 7L is an enlarged view of the barrel needle seal system shown in FIG. 7F.

DESCRIPTION OF THE PREFERRED EMBODIMENTS

There are several preferred embodiments within the instant invention and the preference depends to a great extent on manufacturing and sales choices. The instant invention can be supplied in one of three major forms:

A) hypodermic injection syringe, or
B) hypodermic sampling syringe of two forms:
B1) aspiration filling, which could also inject, or
B2) pressure filling, which could not inject.

There are also several variations for the syringe barrel tip which interact with the three major embodiments and which in themselves increase the overall number of preferred embodiments. There is an alternate syringe barrel design. Finally there are several alternate designs for sealing the retractable hollow needle at the barrel tip and within the hollow plunger. The major embodiments will be discussed in reverse order.

Attention is called to FIGS. 1 through 8 which show the preferred pressure sampler embodiment of the safety syringe. These figures also illustrate a number of the alternative designs which will be discussed in due course. The safety pressure sampler embodiment consists of 10 interrelated parts:

the guide wire/valve assembly (shown generally as 11),
the needle assembly (shown generally as 12),
the plunger assembly (shown generally as 14),
the barrel assembly (shown generally as 15), and
the barrel cap assembly (shown generally as 16).

Figure 1:
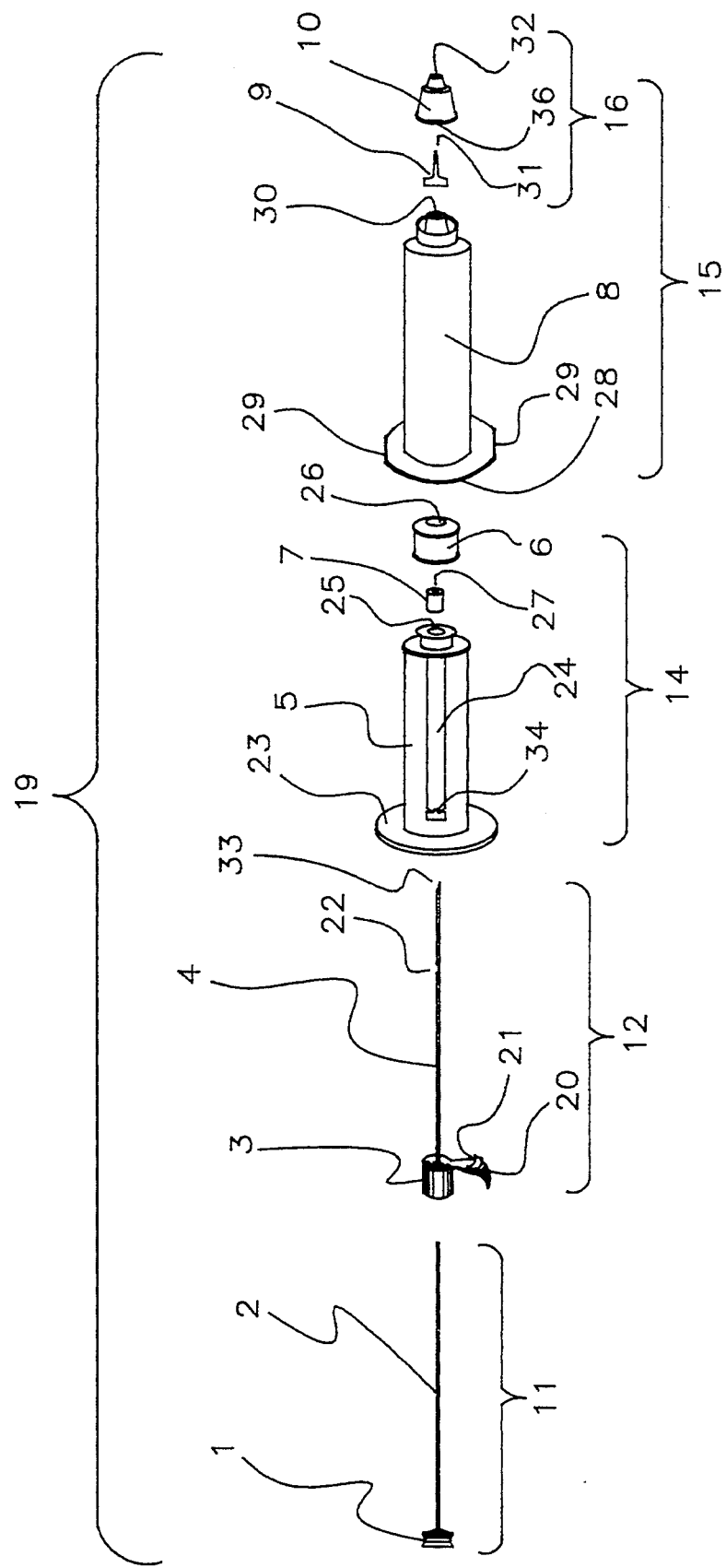
FIG. 1 is an exploded view of the instant invention showing the preferred embodiment.
Figure 2:
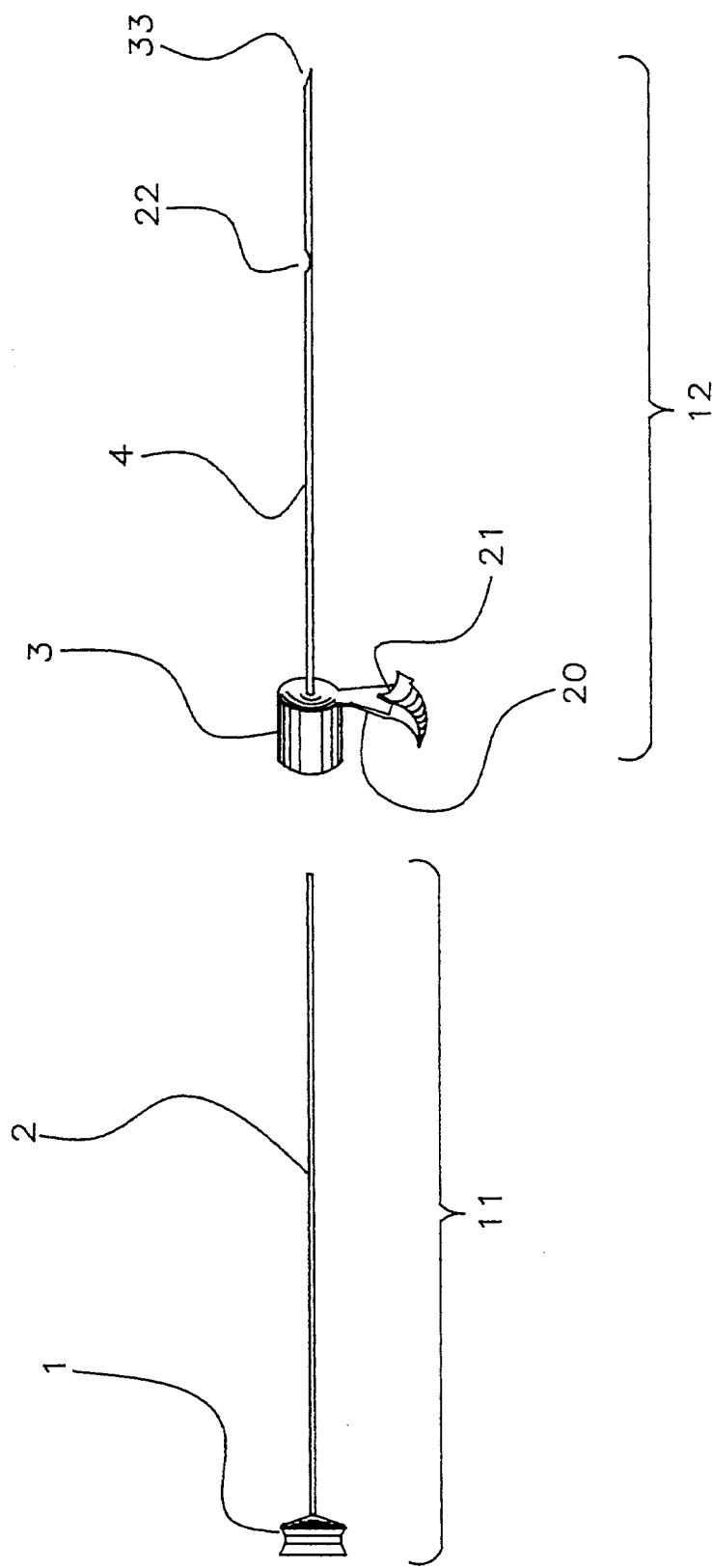
FIG. 2 is an enlarged exploded view showing generally the needle guide wire/valve assembly and the needle assembly.
Figure 3:
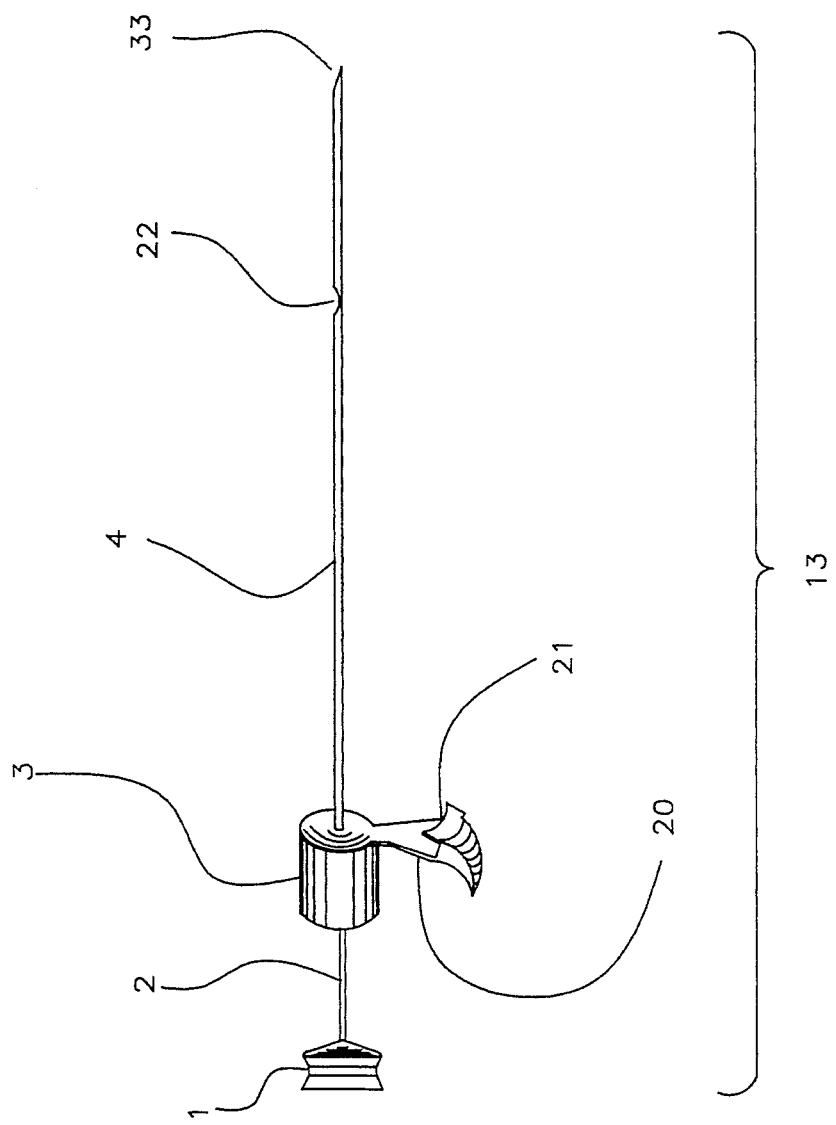
FIG. 3 is an enlarged view of the assembled hollow needle and guide wire/valve assembly.

The operation of the needle guide wire/valve assembly will be explained first. Referring to FIG. 2, the guide wire/valve assembly (generally 11) consists of a guide wire (2) with a cap (1). The guide is sized so that it just fits inside the hollow needle (4) but yet slides easily inside the hollow needle. The hollow needle assembly (generally 12) consists of a needle head (3) with a lever arm (20) and a lever arm latch (21) formed within the lever arm (20). The needle head (3) is attached to the hollow needle (4) and contains an axial opening which aligns with the inside of the hollow needle (4) thus allowing the guide wire (2) to pass through the needle head (3) and into the hollow needle (4). The hollow needle (4) contains a port (22) which is positioned on the hollow needle (4) so that when the needle is fully extended then the port (22) is near or at the bottom of the inside of the syringe barrel. (See FIG. 7.) The hollow needle (4) terminates at its distal end in the standard needle bevel or point (33). Retraction of this point (33) is the purpose of this instant invention.

The guide wire (2) actually serves as a valve and closes off the needle port (22) whenever the wire passes down the needle towards the beveled end (or point) when the hollow needle is retracted. The needle assembly, for the pressure (or even aspirator) sampler, is shown assembled in FIG. 3 (generally 13). Since the guide wire (2) is designed to barely fit within the hollow needle (4), but still be capable of easy movement, the wire will shut off the needle port (22) from the needle bevel (33) whenever the wire passes the port (22) by a reasonable distance. The valve action stems from simple surface tension. The sample fluid exerts surface tension between the wall of the hollow needle (4) and the guide wire (2): this surface tension will stop the movement of fluid. The port (22) and the bevel (33) will be "shut-off". This simple mechanism will stop any fluid from exiting the sample chamber through bevel (33), which will be in the sample chamber whenever the needle is retracted, and out through port (22) into the hollow plunger (5). The same action will stop the sample from becoming contaminated (reverse flow from the port through the bevel). Note how the valve will also stop the fluid sample frown outgasing, thus assuring a true sample when that sample reaches the laboratory.

Note that it might be possible to design or choose a needle length that would keep the bevel port (33) on the outside of the barrel and yet within the confines of the Luer Lock portion of the syringe barrel (8). This device considers this approach but believes that safety requires complete retraction of the hollow needle (4) to within the confines of the barrel.

Figure 4:
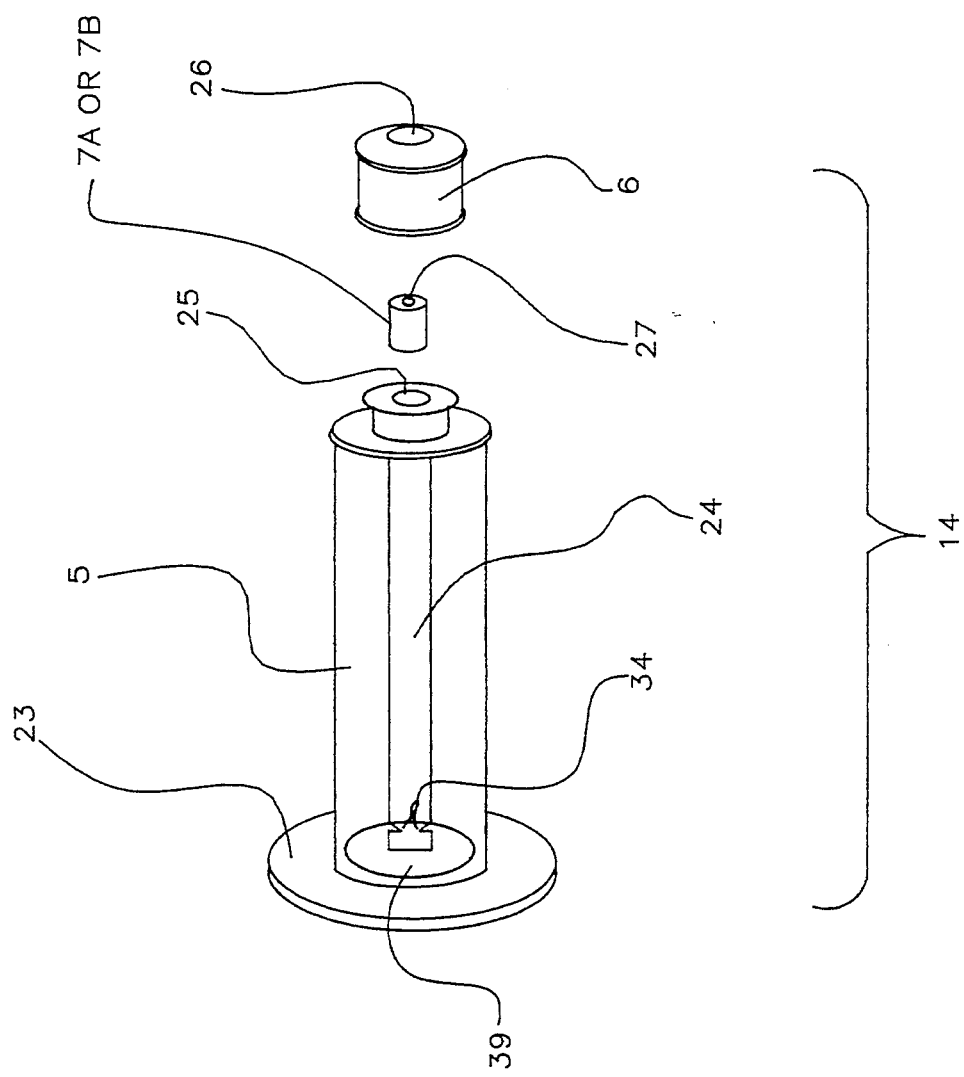
FIG. 4 is an enlarged exploded view of the hollow plunger assembly.

The hollow plunger assembly is shown generally as 14 in FIG. 4. Essentially this plunger functions exactly the same as any standard syringe plunger except that first it is hollow, second it has retraction locking ramps (34), third it has a slot (24), fourth it has an opening for the needle seal system (25) and fifth it has a needle seal system (in general item 7, but specifically 7A or 7B depending on embodiment). Like the normal syringe plunger it has a piston (6) which sets the volume of a pressure sample, draws a vacuum for an aspirated sample or causes a pressure for an injection syringe. The thumb flange (23) allows the thumb to exert the necessary force against the piston or allows the finger to draw the piston backwards within the syringe barrel. Slot (24) is sized to allow lever arm (20) to pass through it. Retraction locking ramps (34) are essentially molded catches that latch against the needle head (3) preventing the needle from being extended once the ramps catch the needle head (3). The needle assembly (generally 12) passes through the opening in the plunger (25) and then through the enlarged plunger needle seal opening (27). The plunger needle seal (generally 7) is retained within the opening (27), against opening (25), and about the needle (4). In the pressure filled sampler embodiment, the plunger needle seal consists of a packing formed of "microfilter" material (7A). Microfilter material is hydrophobic, in that it will allow entrained air to pass readily through it but will swell and stop fluids from passing through it. Thus the microfilter (7A) will seal sample fluids and yet allow the hollow needle (4) to slide up through so that the needle can be retracted.

The completed plunger and retractable needle assembly (generally 18) for the sampler (pressure or aspirated) embodiment is shown in FIG. 5. Assembly is a matter of choice but the method used by the inventor is as follows:

First, insert the hollow needle assembly (12) through the slot (24) and passing the needle through the opening (25): slightly pry, the slot open and press the needle head (3) through the slot and into the hollow center of the plunger.

Second, draw the needle assembly back up into the hollow plunger.

Third, install the plunger needle seal (7) [this could have been done earlier].

Fourth, install the plunger piston (6) [this could have been done earlier].

Finally, install the guide wire/valve (11) assembly by inserting through the plunger opening (39), guiding it through the hollow needle (4). Guide wire head (1) is then force fitted into the plunger opening (39) completing the needle retraction sub-system (generally 18).

Figure 6:
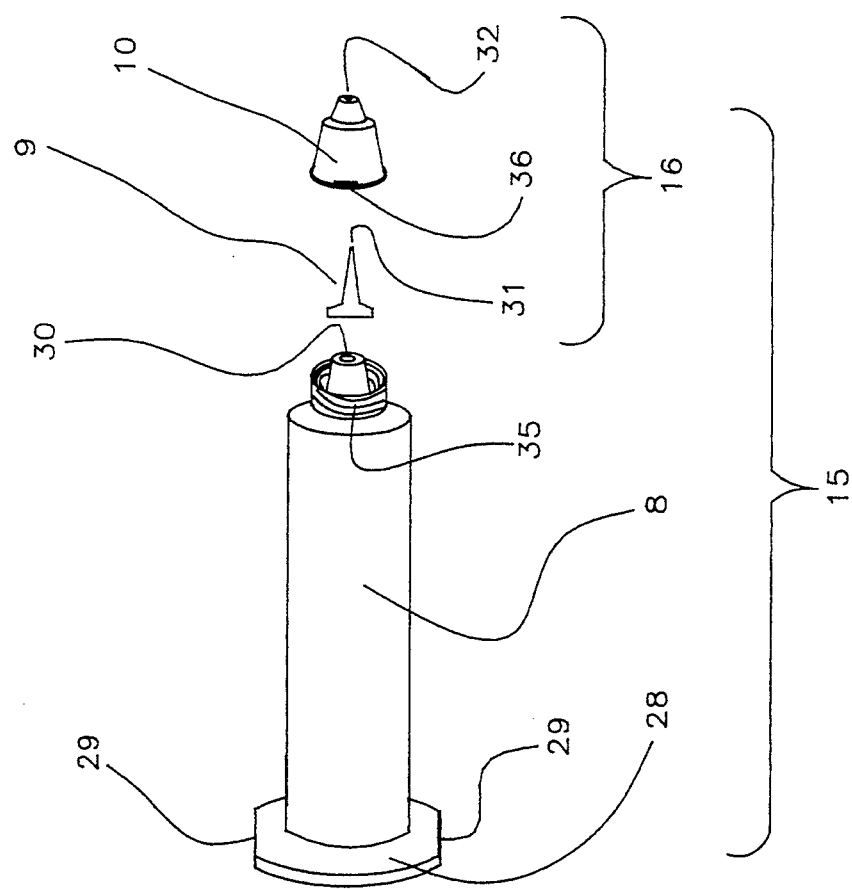
FIG. 6 is an exploded view of a standard barrel assembly showing the finger flange and flat spots on that flange.
Figure 6A:
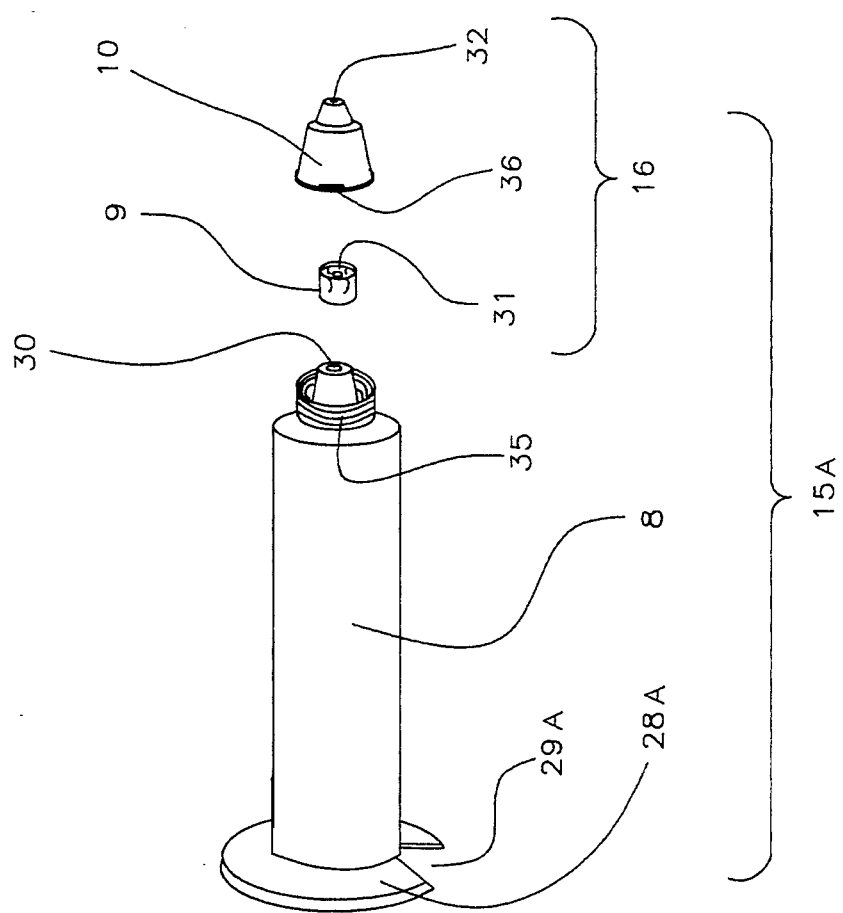
FIG. 6A is all exploded view of an alternate embodiment of a barrel assembly showing the finger flange and the 'pass slot' in that flange.

The barrel assembly (generally 15) shown in FIG. 6 is a standard syringe barrel assembly. A barrel assembly consists of the finger flange (28) with its associated flats (29); the barrel itself (8); and the tip (not numbered) in which there is generally a "Luer Lock" thread (35) for the receipt of a standard needle. An alternate assembly is shown in FIG. 6A; the only difference being in the finger flange (28) design which has a slot (29A) rather then the flats of a standard barrel. The barrel tip (not numbered) also contains a nipple (30) with an opening through which the hollow needle (4) can pass. In this instant invention the barrel assembly also includes a barrel cap sub-assembly (generally 16) which consists of the barrel needle seal (9) and the barrel cap (10). The barrel cap (10) has corresponding Luer Lock Tabs [or flats](36) which allow the cap to be drawn up tight against the barrel nipple via the Luer Lock threads (35) thus forcing the barrel needle seal (9) against the barrel nipple and its opening (30).

Figure 7G:
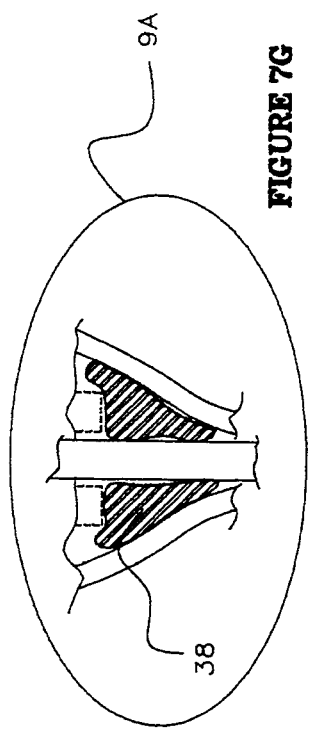
FIG. 7G is an enlarged view of the barrel needle seal system shown in FIG. 7A.
Figure 7A:
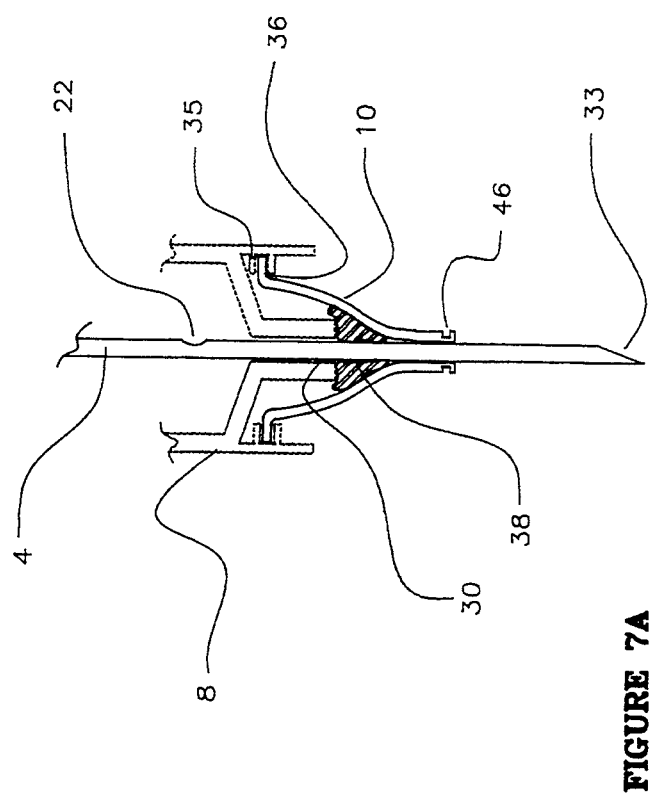
FIG. 7A is a side view of the Pressure Mode Barrel Needle Seal System.
Figure 7I:
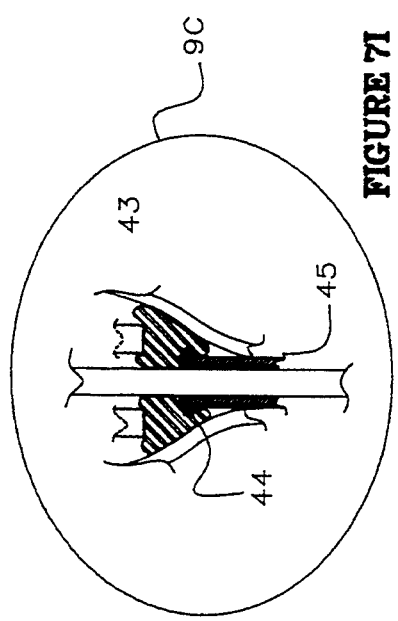
FIG. 7I is an enlarged view of the barrel needle seal system shown in FIG. 7C.

In discussing the pressure sampler and its preferred embodiment, the preferred barrel needle seal assembly is shown in FIG. 7A. FIG. 7A is a cross-section of the barrel cap assembly shown in place on the barrel. The barrel cap (10) is shown with flange (46) which is not necessary for the pressure sampler mode, but is shown as most manufacturers would prefer to make one part for use in all versions of the safety syringe. The cap (10) holds a packing gland (38) in place against the barrel nipple (30). After the hollow needle is placed through opening (30) in the barrel [during assembly], packing gland (38) is squeezed between the barrel nipple and the barrel cap by simply tightening the barrel cap within the Luer Lock. The tightened packing gland (38) then forms the barrel needle seal (9) for the pressure sampler. Experience has shown that a tight seal is needed at the barrel end of the needle to stop fluids from escaping around the needle.

FIG. 7D shows an o'ring variation of the barrel needle valve seal. This alternate embodiment will work for all modes of operation of the safety syringe; however, slight leakage will occur when the needle is retracted. Thus in the sampler modes, a packing gland or self sealing rubber seal must be added to prevent leakage or contamination of the sample when the needle is retracted. The packing gland (38) of FIG. 7A or the rubber tip (41) of FIG. 7B can be utilized. The alternate barrel needle seal assembly consists of the barrel cap (10) with an o'ring seat (46) molded within. An o'ring (47) is placed in the seat and the cap is then placed over the hollow needle (4) and tightened against the barrel using the Luer Lock (35 and 36). It should be realized that the cap (10) will have to be manufactured to fit different sized needles as needed. The preferred embodiment for the pressure sampler barrel cap assembly will fit a number of different sized needles and would be cheaper and simpler to manufacture.

FIG. 7E shows the barrel needle seal assembly moved to within the barrel itself. This variation of the seal also uses an o'ring (49) placed within an o'ring seat (48) molded within the barrel nipple. This variation of the barrel needle seal will function with all embodiments of the safety syringe. The drawback is manufacturing complexity and the fact that the barrel will no longer be a manufactured standard thus increasing its cost.

Figure 8A:
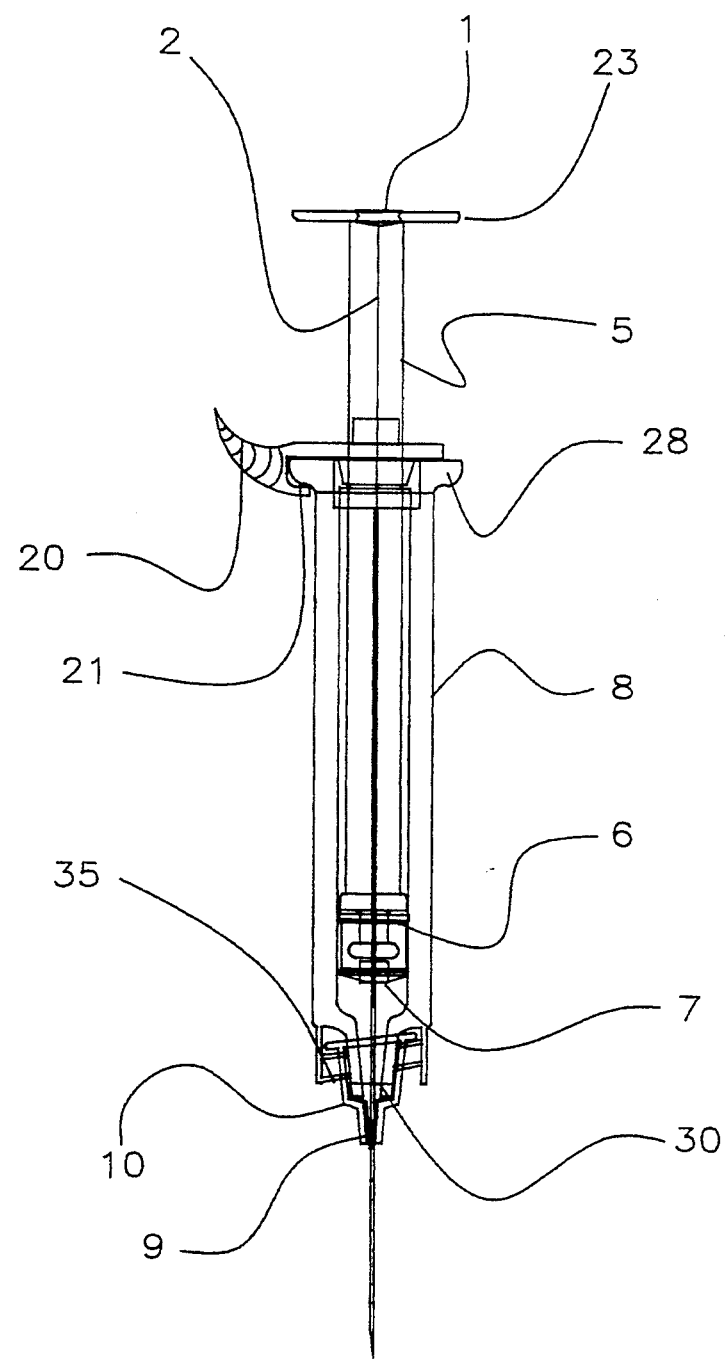
FIG. 8A is a side view of the assembled invention showing the needle extended and locked in place. The plunger is shown in the fully in position.
Figure 8B:
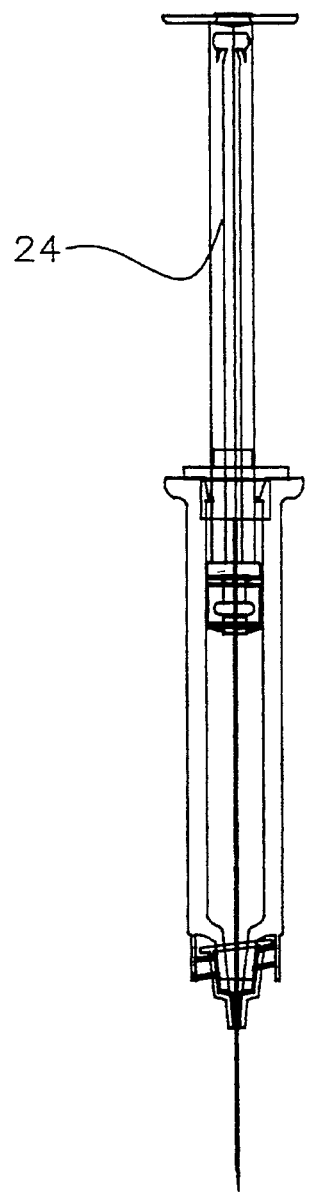
FIG. 8B is a side view of the assembled invention, rotated 90° about its axis, showing the needle extended and locked in place. The plunger is shown in the withdrawn position as if the syringe were being used as a pressure sampler.

The completely assembled pressure sampler is shown in FIGS. 8A through 8D. All that remains is to explain its operation. The pressure sampler as it would appear when removed from its sanitary container is shown in FIG. 8A. The hollow needle (4) is shown in its extended position although it would be possible to package the device with the needle retracted. The hollow needle is latched in its extended position by the lever arm latch (21) located on the lever arm (20). The lever arm latch (21) catches under the finger flange (28) of the barrel and holds the hollow needle (4) extended. In the extended position the needle port (22) is at or near the bottom of the barrel and the guide wire/valve (2) is located above the port (22) thus leaving the port in communication with the needle bevel (33). To use the device in its pressure sampler embodiment, the hollow plunger is withdrawn, as shown in FIG. 8B, to the required sample volume. The sampler is then inserted and arterial pressure will force the blood sample through the bevel (33), through the port (22) and into the barrel. Air (or inert gas) within the barrel will be displaced through the "microfilter" plunger needle seal assembly (7) and into the hollow plunger. That air will then flow out of the plunger slot (24) to the atmosphere. Once the blood sample reaches the "microfilter", it will swell and shut off all flow as well as seal the hollow needle (4) from the hollow plunger (5). That is no fluid will escape past the plunger needle seal (7). The sampler is then withdrawn from the subject, which now exposes the contaminated needle (4) and the needle bevel (33).

The hollow needle (4) is easily retracted to its SAFE position. The worker rotates the plunger assembly so that the needle lever latch (21) is aligned with the barrel finger flats (29). In the alternate embodiment shown in FIG. 6A, the lever latch (21) would be rotated until it aligns with the slot (29A) at which the latch would clear the finger flange (28A). This means that the latch (21) is no longer constrained by the flange and the lever arm

(20) may be pulled upwards towards the top of the hollow plunger (5). The lever arm (20) slides up the hollow plunger (5) via the slot (24) in the plunger. As the hollow needle moves up inside the hollow plunger the needle bevel (33) moves inside the syringe barrel. At the same time the guide wire/valve (2), which is fixed, slides within the hollow needle sweeping sample fluid contained within the hollow needle into the barrel via port (22) which is the shortest flow path. The guide wire/valve (2) will eventually pass port (22) and seal it. The needle port (22) will eventually pass the plunger needle assembly (14) and position itself within the hollow plunger (5). If the port (22) were not valved shut by the needle guide wire/valve (2) fluid could leak into the hollow plunger (5) and come out of the slot (24) and into contact with the world. In a similar manner, the outside world cannot come into contact with the sampled fluid as the communication between the needle port (22) and the bevel (33), which is now within the barrel, is cut off by the guide wire/valve (2). Finally, as the hollow needle (4) retracts past the barrel needle seal assembly (16) the packing gland (38) will close about itself and retain the sample fluid within the barrel.

Figure 8C:
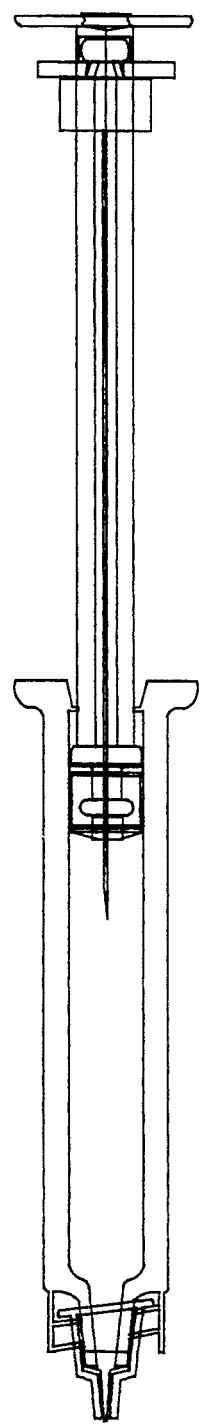
FIG. 8C shows the needle retracted and locked in place inside the hollow plunger.

As the lever arm (20) is drawn upwards within the plunger, the needle head (3) eventually comes in contact with the retraction locking ramps (34). These ramps allow the needle head to slide inside them but do not allow the head to slide out. Thus the retraction ramps (34) permanently latch the needle (4) in a retracted position. It should be apparent that the retraction ramps (34) could be modified to allow a further extension of the needle. The fully retracted and latched needle is shown in FIG. 8C. The sample contained with the barrel is fully isolated from the outside world by the guide wire/valve (2), the plunger needle seal (generally 7) and the barrel needle seal (9). Thus the sample cannot be contaminated nor can the sample leak out and contaminate others.

Figure 8D:
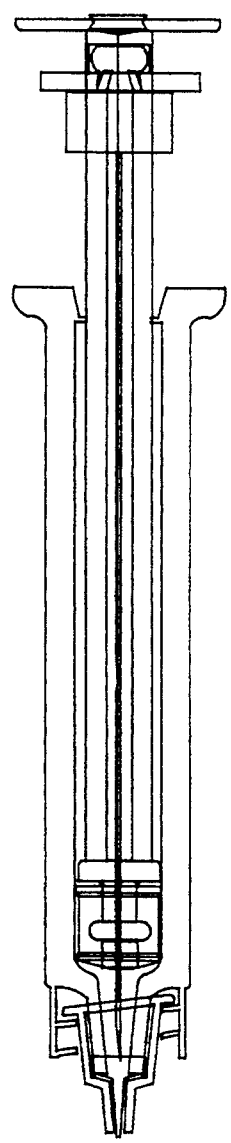
FIG. 8D shows the needle retracted and plunger pushed back into the barrel. This figure illustrates the expulsion of a sample into a Blood Gas Analysis Machine. Note how the retracted needle remains within the confines of the barrel and yet does not interfere with plunger motion.

All that remains is to eject the sample into an analysis machine. This operation is shown in FIG. 8D where the plunger (5) has been pushed back down into the barrel (8) thus forcing the sample fluid out past the barrel seal (7), through the cap (10) and into the machine. If difficulty is experienced in forcing the fluid out the packing gland (38) can be loosen by unscrewing the cap (10) or a special form of the gland which incorporates a check valve could be employed. Note that the retracted hollow needle (4) remains within the syringe and does NOT interfere with the ejection operation.

The alternate variations of the barrel needle seal (9) would work in a similar manner. In the case of o'ring seals (47) in FIG. 7D and (49) in FIG. 7E there could be contamination of the fluid or some fluid could leak out. The problem could easily be solved by adding a resealable rubber covering of the type used in serum vials. In fact a modified self closing o'ring or a packing gland could be used. These systems would increase the cost of manufacture but are not beyond the scope of this invention or disclosure.

Turning now to another major embodiment of the invention which also involves sampling but in the form of aspiration sampling. This technique is similar to pressure sampling except that the sample is drawn from the subject by vacuum within the barrel (8). The vacuum is formed by inserting the sampler with the plunger (5) in the full down position and then slowly withdrawing the plunger (5) until the required sample is drawn into the barrel (8). The only change needed in the preferred embodiment of the pressure sampler previously described is in the plunger needle seal assembly. This seal must be capable of holding a vacuum. Thus the assembly shown in FIG. 4 as item 7B would be a rubber seal rather than the "microfilter" seal (7A). Of course the seal could be an o'ring in a seat molded into the plunger opening (25).

Figure 9:
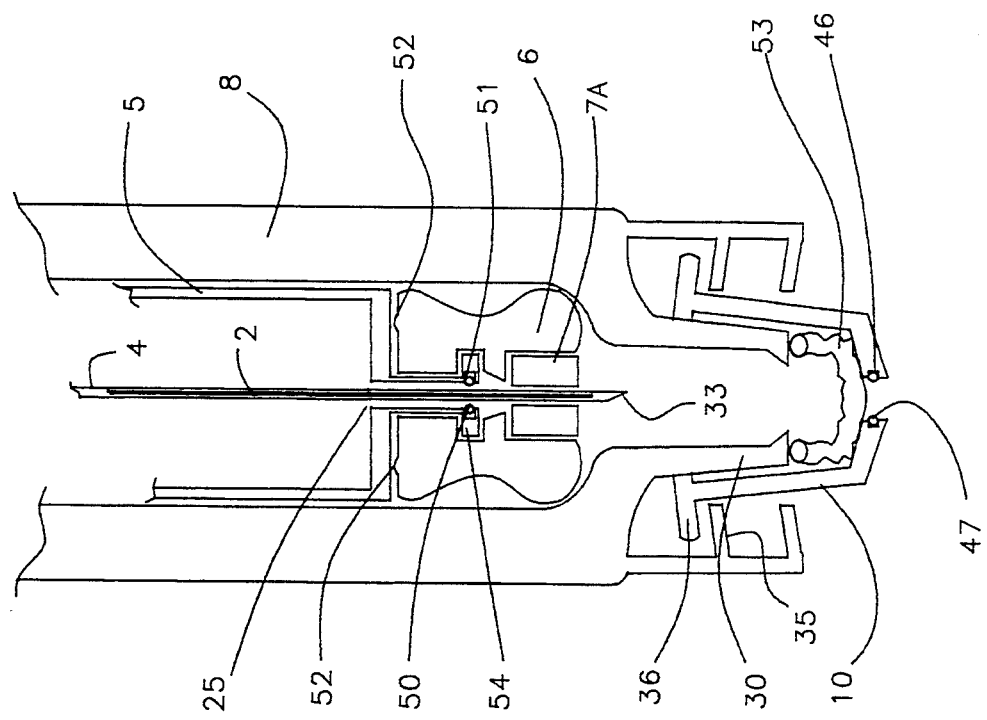
FIG. 9 is a side view of a seal arrangement between the hollow plunger plunger and the hollow needle. This arrangement shows a standard plunger piston modified for use on the hollow plunger: the standard plunger piston shown here will operate in both pressure filled and aspiration samplers. The o'ring seal can similarly be used in the injection mode. Although not shown, the piston could be further modified to retain the o'ring without using a molded lip.

An O'ring seal system for the plunger opening (25) is shown in FIG. 9. An O'ring seat (51) is molded into the plunger opening (25) and an 0'ring (50) is placed in that seat. The piston (6) is shown with a microfilter (7A) and piston spacers (52). This particular embodiment will now function exactly like a presently available sampling syringe which is designed to operate in both the aspiration mode and the pressure mode. When the syringe is operating in the pressure mode, displaced air within the barrel passes through the microfilter (7A) and between the molded hollow plunger (5) and the space caused by the piston spacers (52). When fluid reaches the microfilter, it seals off. To eject the sampled fluid, the plunger is pressed downwards and the piston will press hard against the piston spacers (52) and the plunger lip (54) to form a complete pressure seal. When the syringe is used in the aspiration mode a vacuum must be formed within the barrel when the plunger (5) is withdrawn. This is easily accomplished by the piston (6), for as it is pulled back, the piston moves downward and seals against the plunger lip (54). Thus it can be seen that this invention can operate very easily in conjunction with an existing combination mode (pressure and aspiration) sampler. FIG. 9 also illustrates how an O'ring plunger seal system would operate in the injection mode. It would be possible to mold the o'ring into the needle opening within the piston (6). These various seal system are considered to be within the scope of this invention.

The barrel needle assembly has several more options. The packing gland system of the pressure sampler can still be employed, but the preferred embodiment would be that shown in FIG. 7B. A minor modification or manufacturing step is added to the barrel cap (10). The cap (10) needs a needle guide (42) which is placed inside the cap opening as shown. In addition an outside rubber cap (41) is placed over the outside of the barrel cap (10) and held in place by lip (46). The rubber cap (41) is the same material that is used in serum vials which is a self sealing silicon rubber or equivalent. As vacuum is drawn within the barrel, atmospheric pressure will force the rubber against the hollow needle (4) thus maintaining the seal. After the needle (4) is retracted the rubber cap (41) will self seal and stop any chances of contamination. In a similar manner the barrel needle assemblies of FIGS. 7D and 7E could be used. The problems and limitations discussed under the pressure sampler embodiment would also apply to this variant on the seal.

The operation of the aspiration sampler follows standard procedure. With the needle extended as in FIG. 8A the needle (4) is inserted into the subject. The plunger (5) is then withdrawn and the sample passes up the needle (4) into the barrel (8) in exactly the manner described above. Once the required volume is obtained, the needle (4) is withdrawn from the subject exposing the contaminated bevel (33). The needle (4) is then retracted in the manner described above. The port (22) will seal, the plunger will seal, and the sample will be sealed.

Turning now to the last major embodiment of the instant invention in which the safety syringe is used for pure injection. The syringe would of course be used with the needle (4) extended and the retraction scheme is exactly as previously described. There are some major or minor changes as seen fit. First, the safety syringe does not need the needle port (22) shut off valve as there will be no fluid in the barrel to leak through this port after injection and after retraction of the needle. Second the needle head (3) must be capped (i.e. the opening passing through it must be closed) or the opening should not be present because the guide wire valve assembly is not required.

Figure 5A:
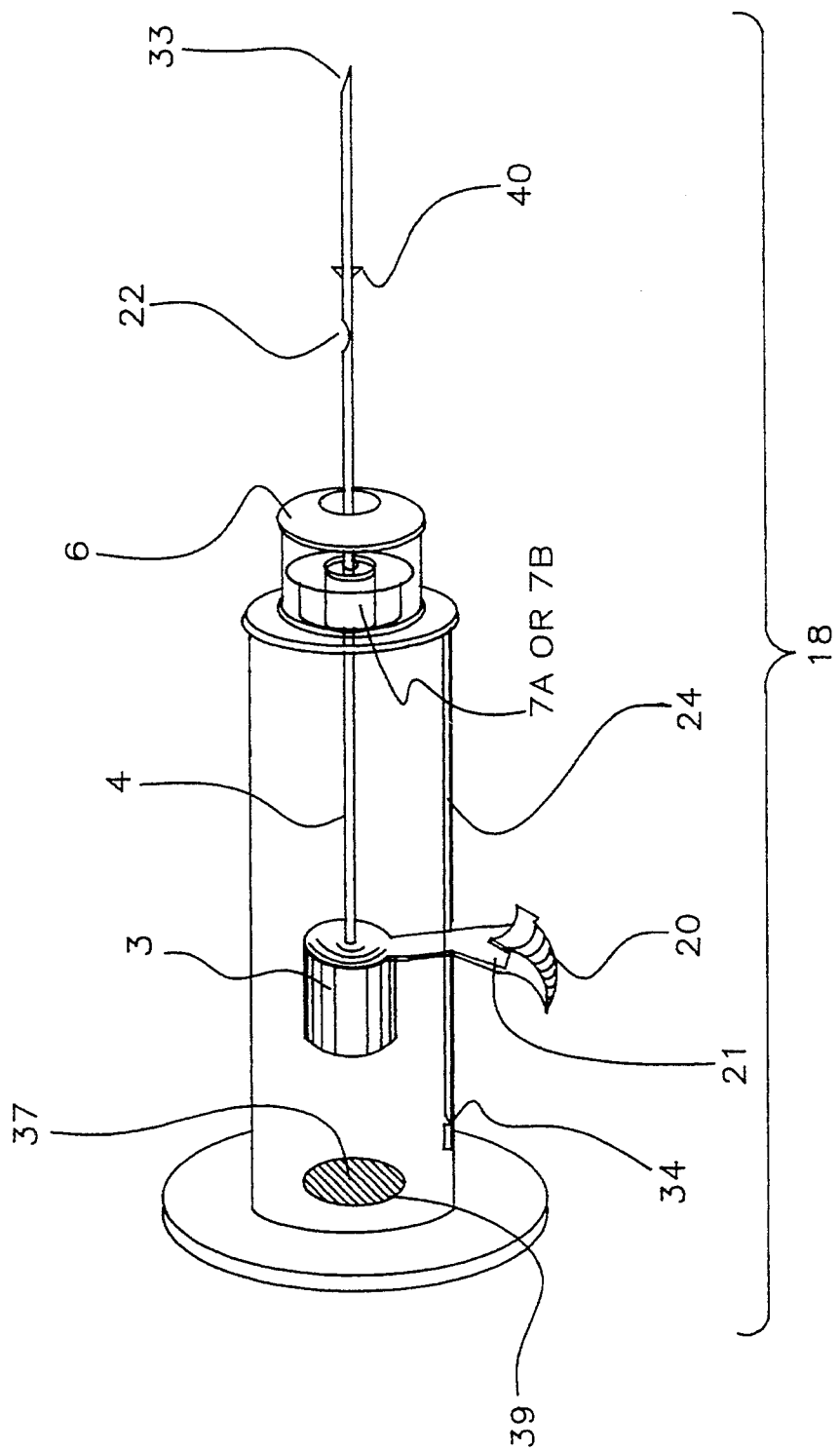
FIG. 5A is a ghost view of an Alternate Embodiment for standard injections and includes only the needle assembly and the 'capped' plunger assembly.

Use of the guide wire valve assembly would be a pure manufacturer's choice—money could be conserved by leaving this assembly out. This embodiment is shown in FIG. 5A. Here the opening in the top of the plunger head or thumb flange (39) could be capped with a plug (37), although this is not strictly necessary, for the comfort of the technician. The plunger needle seal (7B) must be capable of resisting pressure which can be accomplished by a rubber packing or through an o'ring seal. Since injection needles are small there is a possibility of fracture at the needle port (22). Safety barbs (40) will be needed to ensure that a broken needle will come out of the subject. The safety barbs (40) would be designed to catch against the tip of the barrel needle (30) and not be able to pass through it. Thus if a needle does indeed break at the needle port then it will stay attached to the safety syringe.

Figure 7C:
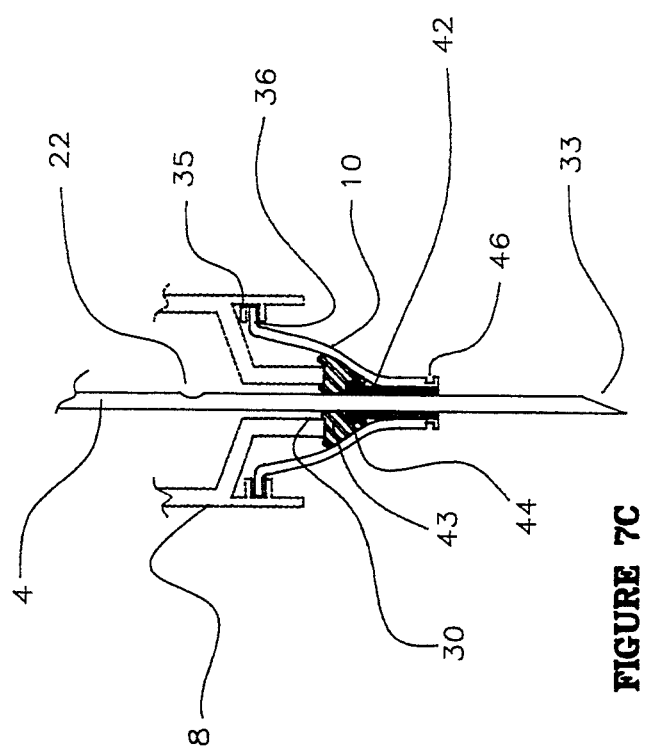
FIG. 7C is a side view of the Injection Mode Barrel Needle Seal System.

The barrel needle seal assembly (16) can take several forms. The original packing gland of FIG. 7A can be used or the o'ring variations of FIGS. 7D and 7E may be employed. The o'ring variations would be ideal in this case as leakage after the needle is withdrawn is not critical nor is there any requirement for sealing of the sample within the barrel [there is nothing in the barrel]. The only disadvantage would be cost. An alternate barrel needle seal assembly is shown in FIG. 7C. This seal assembly also employs a needle guide (45) and resealable rubber gasket (43) as explained for the aspirator sampler. Because the pressure is exerted from within the barrel the resealable rubber gasket (43) must be placed inside the barrel cap (10). The rubber gasket (43) is placed over the needle guide (45) and held in place by tabs (44) on the needle guide. This assembly is placed within the barrel cap (10) which in turn is screwed in place on the Luer Lock (35). The seal assembly is then held in place between the barrel nipple (30) and the barrel cap (10). The hollow needle (4) passes through the rubber gasket (43). Whenever injection pressure is applied to the device the rubber will force up against the hollow needle (4) and seal.

One more variation of the barrel needle seal is illustrated in FIG. 9. Here the barrel cap (10) has an O'ring (47) and an O'ring seat (46) molded into its tip. This O'ring will tightly seal the hollow needle (4). In order to make certain that no sample fluid drips from the barrel and to ensure that the sample fluid cannot be contaminated, a self sealing silicon rubber seal (53) is placed between the barrel nipple (30) and the inside of the barrel cap (10). The action of the Luer lock (35 and 36) will hold this rubber seal in place.

Operation of the safety syringe as an injection syringe would be the same as a regular syringe. The serum would be drawn into the barrel (8) via the needle bevel (33) and the needle port (22) whenever the plunger is withdrawn. The needle would inserted into the subject and serum would flow in the reverse direction whenever the plunger is depressed. After use, the needle would be retracted in the manner already explained.

As can be seen the safety syringe will meet all criteria for a retractable needle safety syringe. The instant invention will serve as a simple injection device and as a sampler device in two modes, pressure or aspiration. The device can serve as its own protector before use by packaging it with the needle retracted. The device can be manufactured from mostly standard syringe components, but variations in seal arrangements are available to improve the device. It would be possible to package the device with preloaded serum or to supply the device "heparinized" when used for Arterial Blood Gas Sampling. It should be apparent that the descriptions in this invention show three uses for the device but the use is only limited by the imagination of the user. The device is designed for medical use but could easily find use in the laboratory; for example, in gas chromatography.

I claim a safety syringe with a retractable needle comprising:

1. A syringe and needle assembly to be configured in a first position with the needle extended for use and a second position with the needle safely retracted, comprising:

a barrel assembly having an elongate hollow tubular barrel with an interior surface and an exterior surface, a longitudinal axis, a first end, and an open second end, having a wall interconnected across said first end of said barrel, said wall having an aperture extending therethrough, having a nipple with an interior surface and an exterior stirface and a first end and a second end, said nipple interconnected at its second end to said wall around said aperture with said first end of said nipple extending outwardly frown said wall, and having a barrel flange interconnected to said barrel at said second end thereof and extending outwardly from said exterior surface of said barrel;

a plunger assembly extending into the interior of said barrel in telescoping relation therewith through said second end of said barrel, including an elongate hollow tubular plunger body with an interior surface and an exterior surface, a longitudinal axis, a closed first end disposed in the interior of said barrel, and a second end extending outwardly from said second end of said barrel, said plunger body having an elongate narrow slot extending from said first end of said plunger body toward said second end through the majority of the length of said plunger body, said slot having a longitudinal axis parallel to said longitudinal axis of said plunger body, and said plunger body having a plunger opening extending through said first end in coaxial alignment with said longitudinal axis of said plunger body, including a plunger flange interconnected to said second end of said plunger body, said plunger flange extending across said second end of said plunger body and extending outwardly therefrom, including needle retraction locking means interconnected to said interior surface of said plunger body near said second end thereof to engage a needle assembly disposed in said plunger body, and including a plunger piston having a piston opening extending therethrough, said plunger piston interconnected to said first end of said plunger body with said piston opening coaxially aligned with and in communication with said plunger opening, said plunger piston in fluid tight sliding relation with said interior surface of said barrel;

a needle assembly including an elongate thin hollow tubular needle greater in length than said barrel, said needle having an interior surface and an exterior surface, an open first end and a second end, and a longitudinal axis, said needle disposed partially in said plunger body with said first end of said needle extending through said plunger opening and said piston opening of said plunger assembly and outwardly therefrom in coaxial alignment therewith, and said needle having a needle port extending from said interior surface to said exterior surface to form a passageway from the interior of said needle to the exterior thereof disposed between said first and second ends of said needle, and a needle head interconnected to said second end of said needle and disposed in said plunger body, and said needle head having a lever arm interconnected to and extending outwardly from said needle head and through said slot of said plunger body with said lever arm generally perpendicular to said longitudinal axis of said needle, said lever arm including lever latching means to be selectively engaged with said barrel flange of said barrel;

a plunger needle seal means disposed in said piston opening of said plunger piston around said needle of said needle assembly to form a fluid tight seal between said plunger piston and said needle; and a barrel needle seal means disposed at said first end of said barrel assembly around said needle of said needle assembly to form a fluid tight seal between said barrel assembly and said needle.

2. The apparatus of claim 1 wherein said plunger needle seal means comprises an o'ring seat concentrically disposed within said piston opening of said plunger piston and an o'ring disposed within said o'ring seat such that said o'ring forms said fluid tight seal between said plunger assembly and said needle.

3. The apparatus of claim 1 wherein said plunger needle seal means comprises an o'ring positioned between said first end of said plunger assembly and said plunger piston such that said o'ring forms said fluid tight seal between said plunger assembly and said needle.

4. The apparatus of claim 1 wherein said plunger needle seal means comprises an o'ring concentrically disposed within said piston opening of said plunger piston, said o'ring being molded as a part of said plunger piston such that said o'ring forms said fluid tight seal between said plunger assembly and said needle.

5. The apparatus of claim 1 wherein said plunger needle seal means comprises a packing gland positioned within said piston opening and extending into said plunger opening with said packing gland restrained by said piston, said packing gland having an aperture in coaxial alignment with said longitudinal axis of said plunger body to receive said needle therethrough such that said packing gland forms said fluid tight seal between said plunger assembly and said needle.

6. The apparatus of claim 1 wherein said plunger needle seal means comprises a microfilter positioned within said piston opening and extending into said plunger opening with said microfilter restrained by said piston, said microfilter having an aperture in coaxial alignment with said longitudinal axis of said plunger body to receive said needle therethrough such that said microfilter forms said fluid tight seal between said plunger assembly and said needle.

7. The apparatus of claim 1, adapted to allow the flow of gas between said needle and said plunger piston and between said plunger piston and said plunger body when said plunger assembly is at rest within said barrel and to prevent such flow of gas when said plunger assembly is moving relative to said barrel, when said barrel is free of liquid, and to seal against such flow of gas when said barrel is filled with liquid between said first end of said barrel and said first end of said plunger assembly, wherein said plunger body further includes a plunger lip interconnected to and disposed outwardly from said first end of said plunger body around said plunger opening:

wherein said plunger piston extends over and is loosely connected to said plunger lip in coaxial relation therewith;

wherein said plunger lip includes an o'ring seat concentrically disposed within said piston opening and an o'ring disposed within said o'ring seat and against said needle so as to form said fluid tight seal between said plunger assembly and said needle:

wherein said plunger piston includes a plurality of piston spacers formed on and extending longitudinally outward from said second end of said plunger piston between said plunger piston and said first end of said plunger body around said plunger opening:

and wherein said plunger piston further includes a microfilter positioned and loosely retained within said conduit in said plunger piston with said microfilter in a dry condition, said microfilter having an aperture through which said needle extends in sealing relation with said microfilter, said microfilter expanding upon contact with liquid so as to become imperious to the flow of gaseous and liquid fluids therethrough and expand to close said piston opening between said plunger piston and said needle and form a fluid tight seal between said plunger piston and said needle within said piston opening.

8. The apparatus of claim 1 wherein said barrel seal means comprises an o'ring seat concentrically disposed within said interior surface of said nipple and an o'ring disposed within said o'ring seat such that said o'ring forms said fluid tight seal between said barrel assembly and said needle.

9. The apparatus of claim 2 wherein said barrel assembly further comprises an open ended annular conduit with an interior surface and an exterior surface and with a first end and a second end, said conduit being of larger cross-sectional diameter than said nipple of said hollow tubular barrel, said conduit interconnected at its second end to said wall of said hollow tubular barrel concentric with said nipple of said hollow tubular panel and extending outwardly from said wall of said hollow tubular barrel, and said conduit having screw threads formed on the interior surface thereof.

10. The apparatus of claim 9, further comprising a barrel cap having a first end, a second end, an outer surface, and a conduit extending through said barrel cap from said first end to said second end to receive said needle therethrough, forming an interior surface of said barrel cap, said second end of said barrel cap having lugs to engage said screw threads on said interior surface of said conduit of said tubular elongated barrel, said barrel cap being generally of conical configuration with said second end of larger diameter than said first end, wherein said barrel seal means comprises an o'ring positioned between said first end of said nipple and said barrel cap assembly to form a fluid tight seal against said needle.

11. The apparatus of claim 9, further comprising a barrel cap having a first end a second end, an outer surface, and a conduit extending through said barrel cap from said first end to said second end to receive said needle therethrough, forming an interior surface of said barrel cap, said second end of said barrel cap having lugs to engage said screw threads on said interior surface of said conduit of said tubular elongated barrel, said barrel can being generally of conical configuration with said second end of larger diameter than said first end, and further having an o'ring seat concentrically disposed within said interior surface of said first end of said barrel cap, wherein said barrel seal means comprises a resealable rubber gasket positioned between said first end of said nipple and said barrel cap such that said resealable rubber gasket forms a first liquid tight seal against said needle when said needle is in a first position extended through said gasket; and such that said resealable rubber gasket reseals when said needle is in a second position retracted from said gasket; and an o'ring disposed within said o'ring seat such that said o'ring forms a second fluid tight seal against said needle when said needle is in said first, extended, position.

12. The apparatus of claim 9, further comprising a barrel cap having a first end, a second end, an outer surface, and a conduit extending through said barrel cap from said first end to said second end to receive said needle therethrough, forming an interior surface of said barrel cap, said second end of said barrel cap having lugs to engage said screw threads on said interior surface of said conduit of said tubular elongated barrel, said barrel can being generally of conical configuration with said second end of larger diameter than said first end, and having an o'ring seat positioned within said interior surface of said first end of said barrel cap, wherein said barrel seal means comprises an o'ring positioned within said o'ring seat such that said o'ring forms a fluid tight seal against and said needle.

13. The apparatus of claim 9, further comprising a barrel cap having a first end, a second end, an outer surface, and a conduit extending through said barrel cap from said first end to said second end to receive said needle therethrough, forming an interior surface of said barrel cap, said second end of said barrel cap having lugs to engage said screw threads on said interior surface of said conduit of said tubular elongated barrel, said barrel cap being generally of conical configuration with said second end of larger diameter than said first end, wherein said barrel seal means comprises a needle guide being axially arranged within said interior surface of said barrel cap about said extended longitudinal axis further having a first end and a second end and having an interior surface and an exterior surface, said second end having a radial ridge positioned on said exterior surface, said second end of said needle guide being near said conical tip of said tubular elongated barrel, and further having a resealable rubber gasket said resealable rubber gasket being positioned over said second end of said needle guide and catching over said ridge on said needle guide such that said resealable rubber gasket forms a liquid tight seal against said needle when said needle is in a first position extended through said gasket, and such that said resealable rubber gasket reseals when said needle is in a second position retracted from said gasket, 14. The syringe and needle apparatus of claim 1 wherein said plunger flange includes a flange opening extending therethrough in coaxial alignment with said longitudinal axis of said plunger body, wherein said needle head includes a head axial opening extending therethrough in coaxial alignment with said needle and in communication with the hollow interior of said needle, and wherein the syringe and needle apparatus further comprises a needle guide wire/valve assembly including a guide wire/valve head interconnected within said flange opening of said plunger flange, and an elongate wire having a longitudinal axis, a first end, and a second end, interconnected at its second end to said guide wire/valve head in coaxial alignment with said plunger body, extending through said head axial opening of said needle head and into the hollow interior of said needle in a fluid tight sliding relation therewith.

15. The apparatus of claim 14 wherein said plunger needle seal means comprises an o'ring seat concentrically disposed within said piston opening of said plunger piston and an o'ring disposed within said o'ring seat such that said o'ring forms said fluid tight seal between said plunger assembly and said needle.

16. The apparatus of claim 14 wherein said plunger needle seal means comprises an o'ring disposed between said first end of said plunger assembly and said plunger piston such that said o'ring forms said fluid tight seal between said plunger assembly and said needle.

17. The apparatus of claim 14 wherein said plunger needle seal means comprises an o'ring concentrically disposed within said piston opening of said plunger piston said o'ring being molded as a part of said plunger piston such that said o'ring forms said fluid tight seal between said plunger assembly and said needle.

18. The apparatus of claim 14 wherein said plunger needle seal means comprises a packing gland positioned within said piston opening and extending into said plunger opening with said packing gland restrained by said piston, said packing gland having an aperture in coaxial alignment with said longitudinal axis of said plunger body to receive said needle therethrough such that said packing gland forms said fluid tight seal between said plunger assembly and said needle.

19. The apparatus of claim 14 wherein said plunger needle seal means comprises a microfilter positioned within said piston opening and extending into said plunger opening with said microfilter restrained by said piston, said microfilter having an aperture in coaxial alignment with said longitudinal axis of said plunger body to receive said needle therethrough such that said microfilter forms said fluid tight seal between said plunger assembly and said needle.

20. The apparatus of claim 14, adapted to allow the flow of gas between said needle and said plunger piston and between said plunger piston and said plunger body when said plunger assembly is at rest within said barrel and to prevent such flow of gas when said plunger assembly is moving relative to said barrel, when said barrel is free of liquid, and to seal against such flow of gas when said barrel is filled with liquid between, said first end of said barrel and said first end of said plunger assembly, wherein said plunger body further includes a plunger lip interconnected to and disposed outwardly frown said first end of said plunger body around said plunger opening;

wherein said plunger piston extends over and is loosely connected to said plunger lip in coaxial relation therewith;

wherein said plunger lip includes an o'ring seat concentrically disposed within said piston opening and an o'ring disposed within said o'ring seat and against said needle so as to form said fluid tight seal between said plunger assembly and said needle;

wherein said plunger piston includes a plurality of piston spacers formed on and extending longitudinally outward from said second end of said plunger piston between said plunger piston and said first end of said plunger body around said plunger opening;

and wherein said plunger piston further includes a microfilter positioned and loosely retained within said conduit in said plunger piston with said microfilter in a dry condition, said microfilter having an aperture through which said needle extends in sealing relation with said microfilter, said microfilter expanding upon contact with liquid so, as to become impervious to the flow of gaseous and liquid fluids therethrough and expand to clause said piston opening between said plunger piston and said needle and form a fluid tight seal between said plunger piston and said needle within said piston opening.

21. The apparatus of claim 14 wherein said barrel seal means comprises an o'ring seat concentrically disposed within said interior surface of said conical nipple and an o'ring disposed within said o'ring seat such that said o'ring forms said fluid tight seal between said barrel assembly and said needle.

22. The apparatus of claim 14 wherein said barrel assembly further comprises an open ended annular conduit with an interior surface and an exterior surface and with a first end and a second end, said conduit being of larger cross-sectional diameter that said nipple of said hollow tubular barrel, said conduit interconnected at its second end to said wall of said hollow tubular barrel concentric with said nipple of said hollow tubular barrel and extending outwardly from said wall of said hollow tubular barrel, and said conduit having screw threads formed on the interior surface thereof.

23. The apparatus of claim 22, further comprising a barrel cap having a first end, a second end, an outer surface, and a conduit extending through said barrel cap from said first end to said second end to receive said needle therethrough, forming an interior surface of said barrel cap, said second end of said barrel cap having lugs to engage said screw threads on said interior surface of said conduit of said tubular elongated barrel, said barrel cap being generally of conical configuration with said second end of larger diameter than said first end, wherein said barrel seal means comprises an o'ring positioned between said first end of said nipple and said barrel cap assembly to form a fluid tight seal against said needle.

24. The apparatus of claim 22, further comprising a barrel cap having a first end, a second end, an outer surface, and a conduit extending through said barrel cap from said first end to said second end to receive said needle therethrough, forming an interior surface of said barrel cap, said second end of said barrel cap having lugs to engage said screw threads on said interior surface of said conduit of said tubular elongated barrel, said barrel cap being generally of conical configuration with said second end of larger diameter than said first end, and further having an o'ring seat concentrically disposed within said interior surface of said first end of said barrel cap, wherein said barrel seal means comprises a resealable rubber gasket positioned between said first end of said nipple and said barrel cap such that said resealable rubber gasket forms a first liquid tight seal against said needle when said needle is in a first position extending through said gasket; and such that said resealable rubber gasket reseals when said needle is in a second position retracted from said gasket; and an o'ring disposed within said o'ring seat such that said o'ring forms a second fluid tight seal against said needle when said needle is in said first, extended, position.

25. The apparatus of claim 22, further comprising a barrel cap having a first end, a second end, an outer surface, and a conduit extending through said barrel cap frown said first end to said second end to receive said needle therethrough, forming an interior surface of said barrel cap, said second end of said barrel cap having lugs to engage said screw threads on said interior surface of said conduit of said tubular elongated barrel, said barrel cap being generally of conical configuration with said second end of larger diameter than said first end, wherein said barrel seal means comprises a packing gland positioned between said first end of said nipple and said barrel cap, said packing gland being restrained by said barrel cap, said packing gland having an aperture coaxially aligned with said longitudinal axis of said barrel, such that said packing gland forms a fluid tight seal against said needle.

26. The apparatus of claim 22, further comprising a barrel cap having a first end, a second end, an outer surface, and a conduit extending through said barrel cap from said first end to said second end to receive said needle therethrough, forming an interior surface of said barrel cap, said second end of said barrel cap having lugs to engage said screw threads on said interior surface of said conduit of said tubular elongated barrel, said barrel cap being generally of conical configuration with said second end of larger diameter than said first end, said first end of said barrel cap further having a radial groove arranged about said exterior surface, said barrel cap further having a needle guide being axially arranged within said interior surface of said barrel cap about said extended longitudinal axis, wherein said barrel seal means comprises a resealable rubber gasket placed over said first end of said barrel cap and catching within said groove on said barrel cap such that said resealable rubber gasket forms a liquid tight seal against said needle when said needle is in a first position extended through said gasket, and such that said resealable rubber gasket reseals when said needle is in a second position retracted from said gasket.

27. A Method of using a safety syringe to inject a fluid into a subject, the safety syringe having a first position with its needle extended and a second position having its needle retracted and having a lever arm, a lever arm latch, retraction locking ramps, a barrel assembly having a barrel flange and a hollow barrel and having a plunger assembly disposed within the hollow barrel, defining a variable volume fluid holding portion of the barrel comprising:

(a) filling the fluid holding portion of the barrel with fluid;

(b) inserting the needle into the subject to receive the fluid;

(c) moving the plunger to reduce the volume of the fluid holding portion of the barrel such that the fluid transfers into the subject;

(d) withdrawing the needle from the subject;

(e) rotating the needle arm such that the lever arm latch clears the barrel flange;

(f) pulling on the needle an such that the lever arm slides upward within the plunger;

(g) clicking the needle head into the retraction locking ramps so that the needle is locked in its retracted position fully disposed within the plunger.

28. A Method of using a safety syringe to inject a fluid into a subject, the safety syringe having a first position with its needle extended and a second position having its needle retracted and having a lever arm, a lever arm latch, retraction locking ramps, a barrel assembly having a barrel flange and a hollow barrel and having a plunger assembly disposed within the hollow barrel, defining a variable volume fluid holding portion of the barrel and further having a needle port in the needle and a needle guide wire/valve within the needle comprising:

(a) filling the fluid holding portion of the barrel with fluid;

(b) inserting the needle into the subject to receive the fluid;

(c) moving the plunger to reduce the volume of the fluid holding portion of the barrel such that the fluid transfers into the subject;

(d) withdrawing the needle from the subject;

(e) rotating the needle an such that the lever arm latch clears the barrel flange;

(f) pulling on the needle arm such that the lever arm slides upward within the plunger whilst the needle guide wire/valve remains stationary so that the needle port is sealed closed by the needle guide wire/valve;

(g) clicking the needle head into the retraction locking ramps so that the needle is locked in its retracted position fully disposed within the plunger.

29. A Method of using a safety syringe to sample a fluid from a subject by pressure, the safety syringe having a first position with its needle extended and a second position having its needle retracted and having a lever arm, a lever arm latch, retraction locking ramps, a barrel assembly having a barrel flange and a hollow barrel and having a plunger assembly disposed within the hollow barrel, defining a variable volume fluid holding portion of the barrel and further having a needle port in the needle and a needle guide wire/valve within the needle comprising:

(a) retracting the plunger to a preselected position within the barrel to set the required sample volume;

(b) inserting the needle into the subject from which the fluid sample is to be drawn;

(c) allowing the fluid sample to enter the barrel assembly whilst allowing any entrained air to escape from the barrel;

(d) withdrawing the needle from the subject;

(e) rotating the needle arm such that the lever arm latch clears the barrel flange;

(f) pulling on the needle arm such that the lever arm slides upward within the plunger whilst the needle guide wire/valve remains stationary so that the needle port is sealed closed by the needle guide wire/valve;

(g) clicking the needle head into the retraction locking ramps so that the needle is locked in its retracted position fully disposed within the plunger;

(h) taking the enclosed sample to a processing station;

(i) expelling the sample by pushing on the plunger.

30. A Method of using a safety syringe to sample a fluid frown a subject by aspiration, the safety syringe having a first position with its needle extended and a second position having its needle retracted and having a lever arm, a lever arm latch, retraction locking ramps, a barrel assembly having a barrel flange and a hollow barrel and having a plunger assembly disposed within the hollow barrel, defining a variable volume fluid holding portion of the barrel and further having a needle port in the needle and a needle guide wire/valve within the needle comprising:

(a) inserting the needle into the subject from which the fluid sample is to be drawn;

(b) retracting the plunger to a given position within the barrel to see the required sample volume;

(c) withdrawing the needle from the subject;

(d) rotating the needle arm such that the lever arm latch clears the barrel flange;

(e) pulling on the needle arm such that the lever arm slides upward within the plunger whilst the needle guide wire/valve remains stationary so that the needle port is sealed closed by the needle guide wire/valve;

(f) clicking the needle head into the retraction locking ramps so that the needle is locked in its retracted position fully disposed within the plunger;

(g) taking the enclosed sample to a processing station;

(h) expelling the sample by pushing on the plunger.

* * * * *